(12) United States Patent
Brenner et al.

(10) Patent No.: US 8,957,204 B2
(45) Date of Patent: *Feb. 17, 2015

(54) PROCESS FOR THE SYNTHESIS OF CYCLIC CARBAMATES

(75) Inventors: Meinrad Brenner, Steg (CH); Erick M. Carreira, Zurich (CH); Nicka Chinkov, Haifa (IL); Miriam Lorenzi, Rheinfelden (CH); Aleksander Warm, Arbaz (CH); Lothar Zimmermann, Brigerbad (CH)

(73) Assignee: Lonza Ltd., Visp (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/879,258

(22) PCT Filed: Oct. 14, 2011

(86) PCT No.: PCT/EP2011/005161
§ 371 (c)(1),
(2), (4) Date: Apr. 12, 2013

(87) PCT Pub. No.: WO2012/048884
PCT Pub. Date: Apr. 19, 2012

(65) Prior Publication Data
US 2013/0217875 A1    Aug. 22, 2013

Related U.S. Application Data

(60) Provisional application No. 61/393,213, filed on Oct. 14, 2010, provisional application No. 61/453,201, filed on Mar. 16, 2011.

(30) Foreign Application Priority Data

Oct. 14, 2010   (EP) .................................... 10013631

(51) Int. Cl.
*C07D 265/18*    (2006.01)

(52) U.S. Cl.
CPC ................... *C07D 265/18* (2013.01)
USPC ............................................. 544/92; 544/90

(58) Field of Classification Search
USPC .......................................................... 544/92
See application file for complete search history.

(56) References Cited

U.S. PATENT DOCUMENTS

2006/0047115 A1    3/2006  Vemishetti et al.
2011/0077397 A1*   3/2011  Gurjar et al. ................... 544/92

FOREIGN PATENT DOCUMENTS

| WO | WO 95/20389 A1  | 4/1995  |
| WO | WO 96/37457 A1  | 11/1996 |
| WO | WO 98/27073 A1  | 6/1998  |
| WO | WO 98/30540 A1  | 7/1998  |
| WO | WO 9830543 A1   | 7/1998  |
| WO | WO 98/51676 A1  | 11/1998 |
| WO | WO 99/61026 A1  | 12/1999 |
| WO | WO 2006/047115 A1 | 5/2006 |
| WO | WO2012/048886 A1 | 4/2012 |
| WO | WO 2012/048887 A1 | 4/2012 |

OTHER PUBLICATIONS

Jiang et al., "Alkynylation of Carbonyl Compounds with Terminal Acetylenes Promoted by ZNC12 and ET3N: Simple, Mild and Efficient Preparation of Propargylic Alcohols", Tetrahedron Letters 43, (2002), pp. 8323-8325.

Jiang et al., "Zn(II)-Mediated Alkynylation-Cyclization of o-Trifluoroacetyl Anilines: One-Pot Synthesis of 4-Trifluoromethyl-Substituted Quinoline Derivatives", J. Org. Chem. 2002, 67, pp. 9449-9451.

International Search Report, PCT/EP2011/005161, Jan. 16, 2012.

* cited by examiner

*Primary Examiner* — Kahsay Habte
(74) *Attorney, Agent, or Firm* — Hoffmann & Baron, LLP

(57) ABSTRACT

The invention is directed to a process for the preparation of a cyclic carbamate starting with a chiral propargylic alcohol and/or a suitable salt thereof, which is reacted with a cyclization agent selected from phosgene, diphosgene, triphosgene and mixtures thereof, and in that the reaction is carried out in the presence of an aqueous base, and a water-immiscible organic solvent, said organic solvent mainly comprising at least one compound selected from $C_{2-5}$-alkyl $C_{2-5}$-carboxylates and mixtures of at least one $C_{2-5}$-alkyl $C_{2-5}$-carboxylate with at least one $C_{5-8}$-alkane. Another aspect of the invention is directed to a process for the synthesis of said cyclic carbamate starting described above, wherein also a process for the preparation of the chiral propargylic alcohol is provided.

29 Claims, No Drawings

PROCESS FOR THE SYNTHESIS OF CYCLIC CARBAMATES

This application is the U.S. National Phase of, and Applicants claim priority from, International Application No. PCT/EP2011/005161 filed Oct. 14, 2011, U.S. Provisional Application No. 61/393,213 filed Oct. 14, 2010, U.S. Provisional Application No. 61/453,201 filed Mar. 16, 2011 and European Patent Application No. 10013631.6 filed Oct. 14, 2010, each of which are incorporated herein by reference.

The invention is directed to a process for the preparation of compounds of formula

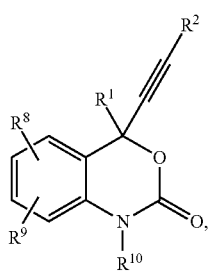

and suitable salts thereof, wherein R1, R2, R8, R9 and R10 are as defined below.

Another aspect of the invention is directed to a process for the synthesis of a chiral propargylic alcohol as the starting compound to produce said cyclic carbamate described above. Some of the cyclic carbamates of formula I are key intermediates for the preparation of pharmaceuticals and agrochemicals and as precursors for compounds in the material sciences.

WO-A-98/27073 provides a cyclisation reaction of the o-aminobenzyl alcohol (SD573) of formula

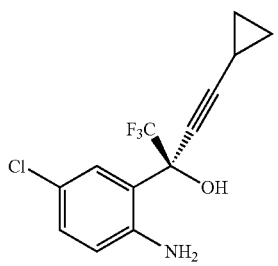 [SMILES: Nc1ccc(Cl)cc1[C@@](O)(C#CC1CC1)C(F)(F)F]

with phosgene in an organic solvent system containing heptanes and tetrahydrofuran to obtain DMP-266 of formula I, wherein $R^1$ is trifluoromethyl, $R^8$ is cyclopropyl, $R^3$ is 6-chloro, $R^9$ is hydrogen and $R^{10}$ is hydrogen. WO-A-98/51676 and WO-A-99/61026 provide a related cyclisation process of such an o-aminobenzyl alcohol with phosgene in a biphasic solvent system comprising methyl tert-butyl ether/water or toluene/water in the presence of potassium hydrogencarbonate.

In the art there are several methods published for the preparation of the compound of formula

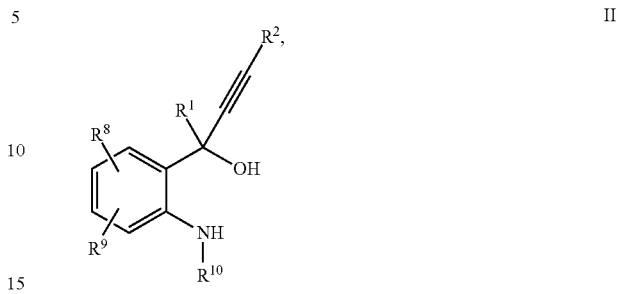

which is the precursor compound before cyclisation. The processes in the art need more than one protic agent and sometimes a high amount of a zinc catalyst. Since the product of the cyclisation is the API (active pharmaceutical ingredient) it is important to reduce heavy metal catalysts as much as possible.

Jiang et al. disclosed in *Tetrahedron Lett.* 2002, 43, 8323-8325 and *J. Org. Chem.* 2002, 67, 9449-9451 the reaction of acetylene derivatives with aldehydes and ketones in the presence of equimolar amounts of a Zn(II) compound to give several racemic propargylic alcohols. Chiral compounds are not mentioned at all.

WO-A-95/20389, WO-A-96/37457, WO 98/30543 and WO 98/30540 disclose several processes for the production of chiral propargylic alcohols useful for the synthesis of pharmaceuticals. WO-A-98/51676 disclose a process wherein by addition of a first chiral and optionally a second additive in a zinc(II) mediated reaction the chiral product is obtained in high enantiomeric excess. The disadvantage of said process is the use of high amounts of expensive zinc catalysts and chiral compounds.

A further task for the present invention was therefore to supply an alternative process for the production of chiral propargylic alcohol with high enantiomeric excess. A further problem was to reduce the amounts of catalyst and other components to be added during the reaction in order to facilitate the workup procedures of the product and to promote industrial production.

The problem to be solved was to supply an alternative process for the production of the compound of formula I in high yield and quality.

The problem is solved by the present invention.

Provided is a process for the preparation of a compound of formula

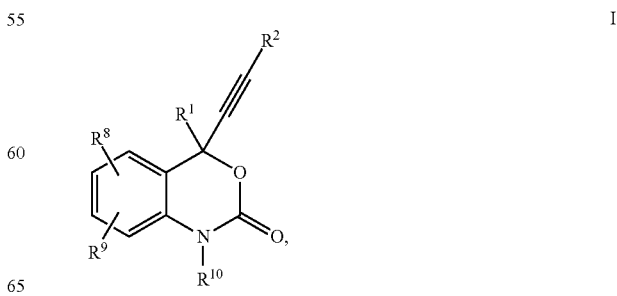

and/or a suitable salt thereof, wherein $R^1$ is selected from the group consisting of hydrogen, linear or branched $C_{1-6}$-alkyl or ($C_{1-6}$-alkoxy)carbonyl, any alkyl or alkoxy optionally being substituted with one or more halogen atoms, $R^2$ is selected from the group consisting of linear or branched $C_{1-6}$-alkyl, ($C_{1-6}$-alkoxy)carbonyl, $C_{3-6}$-alkenyl, $C_{3-6}$-alkynyl and $C_{3-6}$-cycloalkyl, wherein each alkyl, alkoxy, alkenyl, alkynyl and cycloalkyl can carry a further substituent selected from the group consisting of aryl, aralkyl, $C_{1-6}$-alkyl and (1'-$R^3$)—$C_{3-6}$-cycloalkyl, wherein $R^3$ is hydrogen, methyl or ethyl, and wherein any alkyl, cycloalkyl, aryl, and aralkyl is optionally substituted with one or more halogen atoms, cyano, $C_{1-6}$-alkyl, $C_{3-6}$-cycloalkyl, —$NR^4R^5$, —$SR^6$, $S(O)R^6$ or $S(O_2)R^6$, and/or —$OR^7$, with $R^6$ is $C_{1-6}$-alkyl, optionally substituted with one or more halogen atoms, $R^7$ is hydrogen or $C_{1-6}$-alkyl, optionally substituted with one or more halogen atoms, where (a) $R^4$ and $R^5$ are independently selected from hydrogen or $C_{1-6}$-alkyl, or (b) $R^4$ is hydrogen and $R^5$ is $C_{2-7}$-acyl or ($C_{1-6}$-alkoxy)carbonyl, wherein each acyl and alkoxy in $R^5$ in turn is optionally substituted with one or more halogen atoms, or (c) $R^4$ and $R^5$ together with the nitrogen atom form a 5 to 7 membered heterocyclic ring, or (d) $R^4$ and $R^5$ together are =CH-aryl, the aryl moiety optionally being substituted with one or more substituents selected from halogen atoms, —$NH_2$, —$NH(C_{1-6}$-alkyl), —$N(C_{1-6}$-alkyl)$_2$ or $C_{1-6}$-alkyl, or (e) $R^4$ and $R^5$ together are =CH—$N(C_{1-6}$-alkyl)$_2$, $R^6$ is $C_{1-6}$-alkyl, optionally substituted with one or more halogen atoms, and $R^7$ is hydrogen or $C_{1-6}$-alkyl, optionally substituted with one or more halogen atoms, $R^8$ and $R^9$ are independently selected from the group consisting of hydrogen, halogen atom, and $C_{1-6}$-alkyl optionally substituted with one or more halogen atoms, $R^{10}$ is hydrogen or a group selected from the group consisting of aryl, aralkyl, $C_{1-6}$-alkyl and ($C_{1-6}$-alkoxy)carbonyl, wherein the aryl moiety in any aryl or aralkyl is optionally substituted with one or more substituents selected from $C_{1-6}$-alkyl, $C_{1-6}$-alkoxy or $C_{3-8}$-cycloalkyl, each alkyl, alkoxy or cycloalkyl substituent is optionally substituted with one or more halogen atoms, said process comprising the reaction of a compound of formula

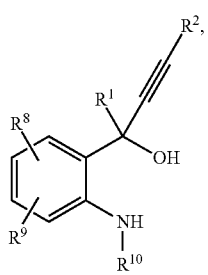

II and/or a suitable salt thereof, wherein $R^1$, $R^2$, $R^8$, $R^9$ and $R^{10}$ are as defined above, with a cyclisation agent selected from phosgene, diphosgene, triphosgene and mixtures thereof, characterized in that the reaction is carried out in the presence of an aqueous base, and a water-immiscible organic solvent, wherein at least 90%-w/w of said organic solvent consisting of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane.

In a preferred embodiment the present method is applicable to optically active compounds of formula II. After the cyclisation the substituents $R^1$ and —C≡C—$R^2$ attached to the carbinol carbon atom of formula I have the same configuration then in the respective compound of formula II.

Here and hereinbelow the term "alkyl" represents a linear or branched alkyl group. By using the form "$C_{1-n}$-alkyl" is meant having 1 to n carbon atoms. $C_{1-6}$-alkyl represents for example methyl, ethyl, propyl, isopropyl, butyl, isobutyl, sec-butyl, tert-butyl, pentyl or hexyl.

Here and hereinbelow the term "alkenyl" represents a linear or branched group carrying at least one carbon-carbon double bound. By using the form "$C_{3-n}$-alkenyl" is meant the main chain of the alkenyl group having 3 to n carbon atoms. $C_{3-6}$-alkenyl represents for example propen-2-yl, propen-3-yl (allyl), buten-1-yl or hexen-1-yl.

Here and hereinbelow the term "alkynyl" represents a linear or branched group carrying at least one carbon-carbon triple bound. By using the form "$C_{3-n}$-alkynyl" is meant the main chain of the alkynyl group having 3 to n carbon atoms. $C_{3-6}$-alkynyl represents for example 1-propynyl, 3-propynyl or 1-hexynyl.

Here and hereinbelow the term "alkoxy" represents a linear or branched alkoxy group. By using the form "$C_{1-n}$-alkoxy" the alkyl group is meant having 1 to n carbon atoms. $C_{1-6}$-alkoxy represents for example methoxy, ethoxy, propoxy, isopropoxy, butoxy, isobutoxy, sec-butoxy, tert-butoxy, pentyloxy and hexyloxy.

Here and hereinbelow the term "$C_{3-n}$-cycloalkyl" represents a cycloaliphatic group having 3 to n ring carbon atoms. $C_{3-8}$-cycloalkyl is selected from the group consisting of cyclopropyl, cyclobutyl, cyclopentyl, cyclohexyl, cycloheptyl and cyclooctyl.

Here and hereinbelow the term "aryl" represents an aromatic or heteroaromatic group, selected from the group consisting of phenyl, naphth-1-yl, naphth-2-yl, furan-2-yl, furan-3-yl, thiophen-2-yl, thiophen-3-yl, benzo[b]furan-2-yl and benzo[b]thiophen-2-yl.

Here and hereinbelow the term "aralkyl" represents a group consisting of an alkyl and an aryl moiety, wherein the alkyl moiety of the aralkyl residue is a $C_{1-8}$ alkyl group and the aryl moiety is selected from the group consisting of phenyl, 1-naphthyl, 2-naphthyl, furan-2-yl, furan-3-yl, thiophen-2-yl, thiophen-3-yl, benzo[b]furan-2-yl and benzo[b]thiophen-2-yl.

Here and hereinbelow the term "$C_{2-5}$-alkyl $C_{2-5}$-carboxylate" represents an carboxylic acid ester consisting of an acyl and an alkoxy moiety, wherein the acyl moiety is selected from acetyl, propionyl, butyryl, isobutyryl, pentanoyl, isopentanoyl, sec-pentanoyl and pivaloyl.

Here and hereinbelow the term "$C_{5-8}$-alkane" represents a linear or branched aliphatic or a cycloaliphatic hydrocarbon having 5 to 8 carbon atoms. In industrial chemistry medium chained aliphatic hydrocarbons such as hexanes, heptanes and octanes often are used as mixtures of the respective linear hydrocarbons together with its branched, i.e. isomeric, forms. Though, n-hexane, n-heptane and n-octane can be used also in pure form.

Here and hereinbelow the term "dialkyl" independently means to alkyl groups attached to a connecting atom. For example in a dialkylzinc (II) compound, two alkyl groups are attached to zinc, whereas in dialkylamino the two alkyl groups are attached to nitrogen.

In contrast to prior attempts it is surprisingly not required to control the pH of the reaction mixture in a certain range, although the formation of by-products is limited while keeping the pH of the aqueous phase at a pH between about pH 6 to 11. Also at a too much acidic pH the compounds of formula I or II might be extracted from the water-immiscible solvent into the aqueous phase. Adjustment of the pH can be carried out for example by pre-charging a suitable base in the reaction vessel and/or by controlled addition of a suitable base, preferably a water miscible and/or soluble base, more preferably an inorganic or organic base selected from the group consisting of alkali or alkaline earth metal carbonates, hydrogencarbonates and hydroxides, piperidine, $C_{1-4}$-alkylpiperidines, pyridine, $C_{1-4}$-alkyl-pyridines, morpholine and tri-$C_{1-4}$-alkylamines. Weak bases such as alkali or alkaline earth metal carbonates, hydrogencarbonates are preferred.

When as compound of formula II, a chiral o-aminobenzyl alcohol is used as a starting compound in the process, the conformation confirmation of the starting compound is maintained in the compound of formula I. In a preferred embodiment the reaction is carried out with compounds where $R^1$ and $R^2$ are not identical.

In a further preferred embodiment in compound of formula II the substituent $R^1$ is $C_{1-4}$-perfluoroalkyl, $R^2$ is cyclopropyl or 1-methyl-cyclopropyl, $R^8$ is a halogen atom in para-position to the amino group, preferably chlorine, $R^9$ is hydrogen and $R^{10}$ is hydrogen.

The reaction preferably is carried out with the free base of formula II as starting compound, though also a salt of said base with an inorganic or organic acid can be used. Suitable salts are for example hydrochlorides, sulfonates, methanesulfonates, oxalates or tartrates. Since the free base of formula II is an amine, usually such salts contain an excess amount of acid. Thus, useful are stoichiometric and non-stoichiometric mixtures and/or salts of the compound of formula II and at least one acid. A preferred salt is a methanesulfonate which comprises about 1:1 to 1.5:1 molar equivalents of methanesulfonic acid to the free amino base of formula II. Where appropriate, an additional amount of the base to neutralize the effect of hydrolysis of an acidic salt has to be taken into consideration, to avoid side reactions since the cyclisation of the present process preferably is carried out at a pH of the aqueous phase between about pH 6 to 11. In case of a strongly acidic salt, such as a methanesulfonate, an additional step to release the free base might be useful. In a preferred embodiment liberating the free base from an acidic salt can be performed in a mixture of a water-immiscible organic solvent and a weak aqueous base, preferably a water miscible and/or soluble base, more preferably an inorganic or organic base selected from the group consisting of alkali or alkaline earth metal carbonates, hydrogencarbonates, phosphates, and hydroxides; ammonium carbonate, hydrogencarbonate, phosphate, and aqueous ammonia; piperidine, $C_{1-4}$-alkylpiperidines, pyridine, $C_{1-4}$-alkylpyridines, morpholine and tri-$C_{1-4}$-alkylamines.

If a salt of the compound of formula II is liberated in an additional step before cyclisation, in a preferred embodiment, the liberation takes place in the same solvent then the cyclisation to allow easy handling. Since the solvent in the present invention is deemed to be water-immiscible, the base liberation can be carried out easily by extracting the organic solvent with an aqueous base.

As outlined above, in a preferred embodiment the organic solvent of the extraction mainly consists of at least one compound selected from $C_{2-5}$-alkyl $C_{2-5}$-carboxylates and mixtures of at least one $C_{2-5}$-alkyl $C_{2-5}$-carboxylate with at least one $C_{5-8}$-alkane. Most preferred solvents are selected from acetates, hexanes, heptanes and mixtures thereof.

In the present process phosgene or its two equivalents diphosgene and triphosgene can be used equivalently as cyclisation agent, either in pure form or as a mixture. By using phosgene, diphosgene and triphosgene as cyclisation agents in the above described process one should be aware that 1 molar equivalent of diphosgene replaces 2 molar equivalents of phosgene, while 1 molar equivalent of triphosgene replaces 3 molar equivalents of phosgene. The reactivity of all three compounds is essentially identical.

Phosgene is a gas, diphosgene is a liquid and triphosgene is a solid at standard conditions (20° C., 1 bar), respectively. Thus, it depends mainly on the desired reaction conditions and local availability which cyclisation agent is used.

In a preferred embodiment in the process as described above the cyclisation agent is provided in gaseous form.

In another preferred embodiment in the process as described above the cyclisation agent is provided in liquid form, either in pure form, as a solution or as a suspension. Phosgene, diphosgene and triphosgene can be dissolved in an aprotic solvent to be provided in liquid form.

In yet another preferred embodiment in the process as described above the cyclisation agent is provided in solid form.

In order to improve workup procedure it might be useful to supply the cyclisation agent in slight excess. In the process as described above, the molar ratio of the cyclisation agent, calculated in molar equivalents of phosgene, to the compound of formula II should be in a range from 1:4, preferably in the range of 1:1 to 2.5:1, more preferably in the range of 1.1:1 to 1.5:1. Generally, the most preferred molar ratio is about 1.2:1. It has to be noted that surprisingly even a large excess of the molar ratio of phosgene equivalents to the compound of formula II 10:1 has almost no negative effect in view of the product formation.

A requirement for the present invention is that the base is a water-miscible and/or -soluble base to allow extraction of the base into the aqueous phase after completion of the cyclisation.

The base used in the reaction can be an inorganic or organic base.

Examples for inorganic bases are alkali or alkaline earth metal carbonates, hydrogencarbonates and hydroxides.

Examples of suitable organic bases are piperidine, $C_{1-4}$-alkylpiperidines, pyridine, $C_{1-4}$-alkylpyridines, morpholine or tri-$C_{1-4}$-alkylamines, wherein any of the alkyl moieties are independently selected from the group consisting of methyl, ethyl, propyl, isopropyl, butyl, isobutyl, sec-butyl and tert-butyl. Using weak bases like alkali or alkaline earth metal carbonates, hydrogencarbonates or a combination of different bases with different $pK_b$ establishes a buffered system. With strong bases like alkali or alkaline earth metal hydroxides a parallel dosage of phosgene and the base might be of advantage.

The process as described above, wherein the weight ratio of water to the organic solvent is in the range from 1:1 to 5:1, preferably in the range from 2:1 to 3.5:1.

In a preferred embodiment at least 90%-w/w of said organic solvent consists of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane.

In a further preferred embodiment at least 95%-w/w, even more preferred at least 98%-w/w, of said organic solvent consists of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane. In another preferred embodiment the water-immiscible organic solvent, consisting of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane.

Compounds forming the maximum 10%-w/w, in a preferred embodiment maximum 5%-w/w and in an even more preferred embodiment maximum 2%-w/w part, of the solvent different from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane, are defined to be additional organic co-solvent. The term "additional organic co-solvent" comprises also mixtures of more than one organic compound.

The additional organic co-solvent is also required to be immiscible with water and shall not act as solubilizer or emulsifier between the aqueous and the organic phase in the reaction mixture. The additional co-solvent must be miscible with the at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane in the presence of water. The additional co-solvent, at least after being solved in the water-immiscible solvent is required to have a lower density than water to avoid separation of the solvents into three phases.

The additional organic solvent may comprise compounds selected from the group consisting of aromatic compounds such as benzene, toluene, substituted naphthalenes, or fully or partially hydrogenated compounds such as decalin or tetralin.

Preferably, the $C_{2-5}$-alkyl $C_{2-5}$-carboxylate is selected from the group consisting of $C_{2-5}$-alkyl acetates, $C_{2-5}$-alkyl propionates, and $C_{2-5}$-alkyl butyrates.

In a further preferred embodiment the $C_{2-5}$-alkyl $C_{2-5}$-carboxylate is selected from the group consisting of $C_{2-5}$-alkyl acetates and $C_{2-5}$-alkyl propionates.

Expediently, the $C_{5-8}$-alkane is selected from the group consisting of pentanes, cyclopentane, hexanes, cyclohexane, heptanes, cycloheptane and octanes.

Even more expediently, the $C_{5-8}$-alkane is selected from the group consisting of hexanes, cyclohexane, heptanes and cycloheptane, preferably from heptanes.

Preferably, the cyclization is carried out at a temperature from −30 to +40° C., even more preferably from 0 to +20° C.

The workup procedures of the compound of formula I for removal of excess phosgene, diphosgene or triphosgene and organic solvents to facilitate crystallization are preferably carried out as known in the art.

According to the invention the product can be obtained with normal liquid-liquid extraction. The product is dissolved as the free base in said organic solvent comprising at least one compound selected from $C_{2-5}$-alkyl $C_{2-5}$-carboxylates and mixtures of at least one $C_{2-5}$-alkyl $C_{2-5}$-carboxylate with at least one $C_{5-8}$-alkane.

After extraction the product can be directly crystallized in the organic solvent. Thus cyclisation, optional liquid-liquid extraction and crystallization can be carried out without any solvent change regarding the organic solvent. Advantageously the crystallization is carried out by seeding the organic solvent comprising the product with seed crystals of the product.

The present process also comprises a new process for the preparation of the compounds of formula II, thus we also claim the preparation of the process as mentioned above, wherein the compound has been obtained by the process as follows. Only the main process as mentioned above is recited. For the avoidance of doubt, all preferred embodiments mentioned above also apply to the following process.

Provided is a process for the preparation of a compound of formula

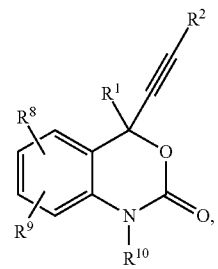

I and/or a suitable salt thereof,
said process comprising the reaction of a compound of formula

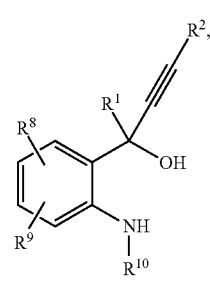

II and/or suitable salts thereof,
wherein $R^1$, $R^2$, $R^8$, $R^9$ and $R^{10}$ are as defined above,
with a cyclisation agent selected from phosgene, diphosgene, triphosgene and mixtures thereof,
wherein the reaction is carried out in the presence of an aqueous base, and a water-immiscible organic solvent, wherein at least 90%-w/w of said organic solvent consisting of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane, and wherein the compound of formula II is obtained by a process comprising the steps of (i) reacting a protic chiral auxiliary with a diorganylzinc(II) compound, in the presence of an aprotic solvent, at a temperature in the range of 0 to 40° C., and (ii) keeping the mixture of step (i), preferably under stirring, in a first maturation period until the reaction is completed, but of at least 20 min, preferably between about 20 to 120 min, and (iii) reacting to the mixture obtained after step (ii) with a compound of formula

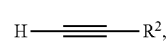

III wherein $R^2$ is as defined above,
(iv) keeping the mixture of step (iii), preferably under stirring, in a second maturation period until the reaction is completed, but of at least 10 min, preferably between about 10 to 120 min, and (v) reacting to the mixture obtained after step (iv) a compound of formula

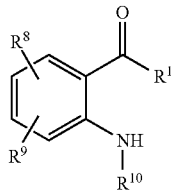

IV wherein $R^1$, $R^8$, $R^9$ and $R^{10}$ are as defined above, and an organolithium base and/or another alkali metal organyl at a temperature in the range of 0 to 40° C., and (vi) keeping the mixture obtained in step (v) to 10 to 50° C. until the reaction is completed, to obtain the compound of formula II.

The major advantages of the present process are the reduction of the zinc(II) catalyst in view of the compound of formula IV, the need of only one protic compound to first react with the zinc(II) catalyst, especially the possibility to avoid addition of fluorinated alcohols.

In contrast to known processes which requires the addition of two different proton sources, wherein an additional proton source can be methanol, ethanol, propanol, isopropyl alcohol, butanol, isobutanol, sec-butanol, tert-butanol, pentanol, $(CH_3)_3CCH_2OH$, $(CH_3)_3CCH(CH_3)OH$, $Cl_3CCH_2OH$, $CF_3CH_2OH$, $CH_2\!=\!CHCH_2OH$, $(CH_3)_2NCH_2CH_2OH$ or even another chiral compound. The present process can be carried out with only one proton source, which at the same time acts as a chiral auxiliary. A preferred proton source in that sense is an ephedrine derivative, more preferably a phenylnorephedrine derivative (PNE derivative).

The present process relies on a specific order of addition of the compounds of the diorganylzinc(II) compound, the compounds of formulae III and IV comprising the two maturation periods of steps (ii) and (iv), respectively. The term "until the reaction is completed" in steps (ii), (iv) and (vi) means that at least 90% conversion, preferably at least 95%, more preferably 98%, is reached in the respective step. The course of conversion can be followed for example by calorimetric measurements, "React IR" or FT-IR. Also possible are off-line methods such as gas chromatography or HPLC. It is possible to establish a correlation between conversion and the output of analytical methods easily with computer aided systems. We suspect that maybe in the first maturation period a first catalytic species if formed, while in the second maturation step a second catalytic species is formed. The first catalytic species might comprise a compound of formula (alkyl)Zn (chiral auxiliary) which might be solved in the mixture or aggregated. The second catalytic species might comprise a compound of formula $(C\!\equiv\!C\!-\!R^2)Zn$(chiral auxiliary), wherein $R^2$ is as defined above. By using diethylzinc ethane evolution of approx. 1 equivalent in respect to diethylzinc could be observed in steps (ii) and (iv), respectively. Ethane formation could be detected during the diethylzinc addition. The ethane release was observed with a delay with respect to the diethylzinc addition. It is assumed that ethane was first dissolved in the reaction solution and then released to the gas phase. $^1$H-NMR analysis shows that some ethane remained dissolved in the reaction mixture. The structures of the catalytic species can be only proposed because of the difficulties to separate the catalytic species from the respective precursors. Especially, since catalytic species would be highly sensitive to air and humidity.

In step (v) the addition of the compound of formula IV and the organolithium base and/or the other alkali metal organyl, are fed simultaneously, either separately or as a mixture. Advantageously, dosage of the organolithium base and/or the other alkali metal organyl starts ahead of the dosage of the compound of formula IV, preferably up to 20 min ahead, more preferably up to about 10 min ahead.

The process is designed to obtain the compound of formula I with an enantiomeric purity (ep) of at least 90%, preferably with an ep of at least 95%, more preferred of at least 96%, and even more preferred of at least 97%.

The protic chiral auxiliary induces the formation of the desired enantiomer during reaction of the compounds of formulae III and IV. The expression "protic chiral auxiliary" means that the chiral auxiliary comprises at least one proton which can be easily removed, most preferred in a hydroxyl group.

In a preferred embodiment the chiral auxiliary is selected from protic N,N-disubstituted ephedrine derivatives.

Suitable protic N,N-disubstituted ephedrine derivatives are for example diastereoisomers of 2-(di-$C_{1-4}$-alkylamino)-1-phenyl-propan-1-ols, such as 2-(dimethylamino)-1-phenyl-propan-1-ol, 2-(diethylamino)-1-phenyl-propan-1-ol, 2-(di-isopropylamino)-1-phenyl-propan-1-ol, and 2-(dibutylamino)-1-phenyl-propan-1-ol; 2-(N,N—$C_{4-6}$-alkylene)-1-phenyl-propan-1-ols, such as 1-phenyl-2-(piperidinyl)propan-1-ol and 1-phenyl-2-(pyrrolidinyl)-propan-1-ol, and 2-(1-heteroaryl)-1-phenyl-propan-1-ols, such as 1-phenyl-2-(1-pyridinyl)-propan-1-ol, 1-phenyl-2-(1-piridinyl)propan-1-ol and. More specific examples are (1R,2S)-2-(dimethylamino)-1-phenyl-propan-1-ol (CAS [552-79-4]), (1S,2R)-2-(dimethyl-amino)-1-phenyl-propan-1-ol (CAS [42151-56-4]), (1R,2R)-2-(dimethylamino)-1-phenyl-propan-1-ol (CAS [14222-20-9]), (1S,2S)-2-(dimethylamino)-1-phenyl-propan-1-ol (CAS [51018-28-1]), (1R,2S)-1-phenyl-2-(pyrrolidinyl)propan-1-ol (CAS [127641-25-2]), (1S, 2R)-1-phenyl-2-(pyrrolidinyl)propan-1-ol (CAS [123620-80-4]=(1S,2R)-PNE), (1R,2R)-1-phenyl-2-(pyrrolidinyl) propan-1-ol and (1S,2S)-1-phenyl-2-(pyrrolidinyl)-propan-1-ol.

In a preferred embodiment the protic chiral auxiliary is (1R,2S)-phenylnorephedrine ((1R,2S)-PNE (1R,2S) 1-phenyl-2-(pyrrolidinyl)propan-1-ol) to obtain ((S)-2-(2-amino-5-chlorophenyl)-4-cyclopropyl-1,1,1-trifluorobut-3-yn-2-ol (SD573) or one of its salts, from 1-(2-amino-5-chlorophenyl)-2,2,2-trifluoroethanone and cyclopropylacetylene.

The amount of the zinc(II) catalyst needed in the reaction can be reduced remarkably compared to processes known in the art. It must be noted that the amount of the zinc(II) catalyst can be surprisingly much lower than the amount of the chiral auxiliary.

In a preferred embodiment the molar ratio of the protic chiral auxiliary to the diorganylzinc(II) compound is in the range of 1.5:1 to 1:1, preferably in the range of 1.3:1 to 1.2:1, most preferred at about 1.24:1.

The chiral auxiliary mediates the catalytic process. Although one would expect that zinc(II) catalyst and the protic chiral auxiliary form a zinc(II) complex with a certain stoichiometry it is not necessary to add the chiral auxiliary and the zinc(II) catalyst in equimolar amounts. Preferably the amount of the chiral auxiliary is slightly higher than the amount of the diorganylzinc(II) catalyst.

Suitable diorganylzinc(II) compounds are for example selected from di($C_{1-8}$-alkyl) and di($C_{3-6}$-cycloalkyl), wherein the alkyl moieties are selected from the group consisting of methyl, ethyl, propyl, isopropyl, butyl, isobutyl, sec-butyl and tert-butyl, pentyl, hexyl, heptyl, and octyl, and wherein the cycloalkyl moieties are selected from the group consisting of cyclopropyl, cyclobutyl, cyclopentyl and cyclohexyl.

In another embodiment the diorganylzinc(II) compound is diphenylzinc or $Zn(OTf)_2$, wherein OTf denotes a "triflate" (trifluoromethanesulfonate) group.

In a preferred embodiment in step (i) the molar ratio of the protic chiral auxiliary to the compound of formula III is in the range of 1:1 to 1:10, preferably in the range of 1:2 to 1:6, more preferably of 1:3 to 1:6.

Addition of the compound of formula III can be carried out at a temperature from 0 to +40° C., preferably from +10 to about +30° C.

In a preferred embodiment the compound of formula III is selected from the group consisting of terminal $C_{3-8}$-alkyla-lkynes, cyclopropylacetylene, (1'-methyl)-cyclopropyl-acetylene and phenylacetylene.

It is recommended, that in step (iii) the compound of formula III is used in a molar ratio to the compound of formula IV of 1:0.6 to 1:1.3

In a further preferred embodiment the organolithium base is added in a molar ratio to the compound of formula III in the range of 1:0.8 to 1:1.5, preferably of 1:0.8 to 1:1.2.

A suitable organolithium base in the present process is selected from the group consisting of ($C_{1-6}$-alkyl)lithium, lithium diisopropylamide (LDA), lithium hexamethyldisilazide (LiHMDS), phenyllithium, and naphthyllithium.

Preferably the organolithium base is an organolithium compound or a lithium organic salt.

In preferred embodiment such organometallic lithium compound is selected from the group consisting of phenyllithium and ($C_{1-6}$-alkyl)lithium.

Preferably said ($C_{1-6}$-alkyl)lithium is selected from the group consisting of methyllithium, n-butyllithium, sec-butyllithium, tert-butyllithium, and hexyllithium.

In a further preferred embodiment the lithium organic salt is a lithium $C_{1-6}$-alkoxide.

Preferably the other alkali metal organyl is selected from sodium or potassium $C_{1-6}$-alkoxides, sodium or potassium diisopropylamine, and sodium or potassium hexamethyldisilazide.

The organolithium base and/or the other alkali metal organyl can be used either independently or in mixtures of at least two different species.

During the addition of the organolithium base and/or the other alkali metal organyl the reaction mixture is preferably kept at a temperature from about +10 to +30° C.

In the present process the aprotic solvent preferably is selected from the group consisting of aprotic non-polar solvents, aprotic polar solvents and mixtures thereof.

The solvents of agents added in solution may be selected independently of each other. Particularly preferred the solvent is selected from the group consisting of tetrahydrofuran, benzene, chlorobenzene, o-, m-, p-dichlorobenzene, dichloromethane, toluene, o-, m-, and p-xylene, hexanes, heptanes, cyclohexane, pentane, 1,4-dioxane, cyclohexane, diethyl ether, tert-butyl methyl ether, diisopropyl ether, N-methylpyrrolidine, and mixtures thereof.

EXAMPLES

The chiral alkynylation reaction (Examples 1, 2, and 4) was performed two times with the respective starting compounds. Once using (1R,2S)-1-phenyl-2-(pyrrolidinyl)propan-1-ol ((1R,2S)-PNE) as ligand and once using (1S,2R) 1-phenyl-2-(pyrrolidinyl)propan-1-ol ((1S,2R)-PNE) as ligand. This allowed the unambiguous assignment of the two enantiomers of the products by HPLC. In the experimental details below, only the experiments using (1S,2R)-PNE are described in detail because there was no major difference between (1R, 2S)-PNE and (1S,2R)-PNE. For the all examples using cyclopropylacetylene addition to a diethylzinc catalyst, an ethane release could be observed as well as described in Example 1. The configuration of the products of example 2 to 4 were tentatively assigned based on the assumption that reaction in presence of ligand (1S,2R)-PNE gives preferably the product with (R)-configuration in analogy to Example 1 (SD573 process), where the configuration of both enantiomers are well known. In the SD573 process (1R,2S)-PNE gives preferably the product with (S)-configuration. Procedures for analytical methods A to D are attached after the examples.

In all cyclisation examples, except where not expressively mentioned, the ee was not measured since in all cyclisation examples with final ee-measurement the product (for example DMP-266) always corresponded to the ee of the respective starting compound, for example in case of cyclisation of SD573-MSA or SD573 free base (CAS [209412-27-7], 99.6% ee) to DMP-266.

ee=enantiomeric excess=$((S)-(R))/((S)+(R))$ ep=enantiomeric purity=$(S)/((S)+(R))$ Example 1

S)-2-(2-Amino-5-chlorophenyl)-4-cyclopropyl-1,1,1-trifluorobut-3-yn-2-ol mesylate (2:3 mol/mol) (SD573-MSA A solution of (1R,2S)-PNE (18.1%-w/w, 171.6 g, 151 mmol) in a THF/toluene mixture (9:1-w/w) was charged in a vessel and cooled to 17° C. A solution of diethylzinc in toluene (29%-w/w, 52.0 g, 122 mmol) was added at 15 to 20° C. and the mixture was aged at said temperature for 30 min. Ethane (approx. 1 equivalent in respect to diethylzinc) was formed during the diethylzinc addition and partially released from the reaction mixture. The ethane release is observed with a delay with respect to the diethylzinc addition, since ethane is first dissolved in the reaction solution and then released to the gas phase. According to $^1$H-NMR analysis some ethane remained dissolved in the reaction mixture. A solution of cyclopropylacetylene (compound of formula III, wherein $R^2$ is cyclopropyl) in toluene (70%-w/w, 57.0 g, 600 mmol) was added at 15 to 20° C. and the resulting mixture was aged at 20° C. for 1 h. During the addition of cyclopropylacetylene additional ethane (approx. 1 equivalent in respect to diethylzinc) was formed and released to the gas phase. A solution of butyllithium (BuLi) in toluene (157.6 g, 2.92 mol/kg, 460 mmol) and a solution of 1-(2-amino-5-chlorophenyl)-2,2,2-trifluoroethanone (SD570, compound of formula IV, wherein $R^1$ is trifluoromethyl, $R^8$ is 5-chloro, $R^9$ is hydrogen and $R^{10}$ is hydrogen) (40.1%-w/w, 278.0 g, 500 mmol) in THF/toluene (1:1-w/w) were added in parallel to the reaction mixture at 20° C. within 180 min. The addition of BuLi was started 10 min in advance of the SD570 addition. Butane was formed during BuLi addition. However, most of the butane remained dissolved in the reaction mixture and only weak gas formation was observed. The course of reaction can be followed online, for example by calorimetric measurements or by "React IR" also called "in-situ FTIR". After complete addition of SD570 the reaction mixture was stirred for 30 min at 20° C., then heated to 30° C. over a period of 60 min and aged for 6 h at 30° C. The reaction mixture was stirred at 0° C. overnight, diluted with toluene (218 g) at 20° C. and quenched by addition of aqueous citric acid (1 M, 375 g). After stirring for 15 min the phases were separated and the aqueous phase was discarded. The organic phase was successively washed with water (76 g), aqueous NaHCO$_3$ solution (5%-w/w, 200 g), and again water (100 g). The organic phase was partially concentrated, then diluted with toluene (250 g), again partially concentrated and diluted with toluene (976 g residue). The enantiomeric purity (ep) of (S)-2-(2-amino-5-chlorophenyl)-4-cyclopropyl-1,1,1-trifluorobut-3-yn-2-ol (SD573) in the crude product was approx. 96 to 97% according to Method B. Although not belonging to the preparation process, described is also a process to transfer the product in a more stable form as a methanesulfonic acid salt. The residue was diluted with isopropyl alcohol (126.6 g). Then methanesulfonic acid (43.3 g) was added over a period of 30 min at 30° C. Seeding crystals (between 1 and 10 mg) were added and the mixture aged for 30 min at 30° C. A second portion of methanesulfonic acid (26.5 g) was added over a period of 60 min at 30° C. The resulting solution was aged for 30 min at 30° C. and later cooled to 5° C. over a period of 60 min. After further aging at 5° C. for 30 min, the product was filtered and washed with cold toluene/isopropyl alcohol (10:1-w/w, 262 g) at 5° C. The wet methanesulfonic acid salt of SD573 ((S)-2-(2-amino-5-chlorophenyl)-4-cyclopropyl-1,1,1-trifluorobut-3-yn-2-ol mesylate (2:3 mol/mol, SD573-MSA, compound of formula II, wherein R$^1$ is trifluoromethyl, R$^2$ is cyclopropyl, R$^8$ is 5-chloro, R$^9$ is hydrogen and R$^{10}$ is hydrogen) was dried in vacuo at 40° C. to obtain 188.3 g (432 mmol, 86.5% yield). SD573-MSA was obtained with a purity of 99.9% and 99.7% ep, according to Method A.

Example 2

R)-2-(2-Aminobiphenyl-3-yl)-4-cyclopropyl-1,1,1-trifluorobut-3-yn-2-ol methanesulfonate (1:1 mol/mol (1S,2R)-PNE (20.3 g, 18.0 mmol) in THF/toluene (9:1-w/w, 18.2%-w/w) was charged under a nitrogen atmosphere to a dry, jacketed 150 mL-reactor with agitator. Diethylzinc in toluene (29.9%-w/w, 6.48 g, 15.7 mmol) was added by syringe keeping the temperature at 17 to 22° C. and the mixture was aged for 30 min at 17° C. Cyclopropylacetylene in toluene (69.6%-w/w, 6.84 g, 72.0 mmol) was added at 17° C. and the resulting mixture was aged for about 60 min at 20° C. To the reaction mixture BuLi in toluene (3.06 mol/kg, 19.9 g, 60.9 mmol) and (1-(4-aminobiphenyl-3-yl)-2,2,2-trifluoroethanone (CN46225, compound of formula IV, wherein R$^1$ is trifluoromethyl, R$^8$ is 5-phenyl, R$^9$ is hydrogen and R$^{10}$ is hydrogen) (43.0%-w/w, 37.0 g, 60 mmol) in THF/toluene (1:1-w/w) were added in parallel over a period of 3 h at 20° C. The addition of BuLi was started about 10 min in advance of the CN46225 addition. After complete addition of BuLi and CN46225, the reaction mixture was stirred for 30 min at 20° C., then heated over a period of 1 h to 30° C. and aged for 6 h at 30° C. The reaction mixture was stirred overnight at 0° C. HPLC indicated 94.3% conversion and 95.6% ep, according to Method B. The reaction mixture was diluted with toluene (27.6 g) at room temperature and quenched by adding aqueous citric acid (1 M, 45.3 g). The phases were separated and the aqueous phase was discarded. The organic phase was successively washed with water (9.1 g), aqueous NaHCO$_3$ (5%-w/w, 24.2 g) and water (12.0 g). The organic phase was heated under reduced pressure to partly remove THF while toluene is added to finally reach a THF poor residue (54.5 g) of (R)-2-(4-aminobiphenyl-3-yl)-4-cyclopropyl-1,1,1-trifluorobut-3-yn-2-ol (CN46630, compound of formula II, wherein R$^1$ is trifluoromethyl, R$^2$ is cyclopropyl, R$^8$ is 5-phenyl, R$^9$ is hydrogen and R$^{10}$ is hydrogen). The residue was diluted with isopropyl alcohol (16.7 g) and toluene (60.0 g). A first portion of methanesulfonic acid (5.48 g, 57.0 mmol) was added by a syringe pump over a period of 30 min at 30° C. Seeding crystals (a small portion between 1 and 10 mg) were added and the mixture was aged for 30 min at 30° C. A second portion of methanesulfonic acid (2.88 g, 30.0 mmol) was added by syringe pump over a period of 45 min at 30° C. The mixture was stepwise aged and cooled over 1 h 45 min to finally reach 5° C. The product was filtered, and the filter cake was washed with toluene/isopropyl alcohol (10:1-w/w, 27.0 g) and dried in vacuo at 40° C. The dry product (R)-2-(4-aminobiphenyl-3-yl)-4-cyclopropyl-1,1,1-trifluorobut-3-yn-2-ol methanesulfonate (1:1 mol/mol, CN46630-MSA) (15.2 g, 35.6 mmol, 59% yield) was obtained as an off-white solid (99.4% purity and 99.7% ep, according to Method B). The combined mother liquor and wash liquor was concentrated (46.7 g residue). During storage overnight at 3° C. a white solid crystallized from the residue. The product was filtered, washed with toluene, and then toluene/isopropyl alcohol (10:1-w/w, 10 g) was added. After stirring the slurry for 60 min at 30° C. the mixture was cooled to 3° C. and filtered. The product was washed with toluene/isopropyl alcohol (10:1-w/w) and dried in vacuo at 40° C. CN46630-MSA (second crop, 3.8 g, 8.0 mmol, 13% yield) was obtained as off-white solid (89.7% purity at 99.7% ep, according to Method B).

Example 3

(R)-4-(Cyclopropylethynyl)-6-phenyl-4-(trifluoromethyl)-1,4-dihydro-2H-3,1-benzoxazin-2-one (R)-2-(4-Aminobiphenyl-3-yl)-4-cyclopropyl-1,1,1-trifluorobut-3-yn-2-ol methane-sulfonate (CN46630-MSA) of example 2 (14.7 g, 34.4 mmol) in ethyl acetate/heptanes (1:1 v/v, 27.9 g) was charged in a jacketed 150 mL-reactor with agitator and off-gas scrubber with caustic soda. After addition of aqueous Na$_2$CO$_3$ (12%-w/w, 32.3 g, 36.4 mmol, formation of gas during addition!) the mixture was stirred for 15 min at 15° C. The aqueous phase was separated and discarded. Aqueous Na$_2$CO$_3$ (12%-w/w, 41 g, 46 mol) and ethyl acetate (20 g) were charged to the organic phase. Triphosgene (4.41 g, 14.9 mmol) was added in portions over a period of 25 min at 10° C. The reaction mixture was stirred for 2 h at 8° C. The mixture was diluted with ethyl acetate (45 g) and the phases were separated. The aqueous phase was discarded. The organic phase was washed with water (12 mL), dried over MgSO$_4$, filtered and concentrated and dried at 50° C. under reduced pressure to obtain (R)-4-(cyclopropylethynyl)-6-phenyl-4-(trifluoromethyl)-1,4-dihydro-2H-3,1-benzoxazin-2-one (CN46685, compound of formula I, wherein R$^1$ is trifluoromethyl, R$^2$ is cyclopropyl, R$^8$ is 6-phenyl, R$^9$ is hydrogen and R$^{10}$ is hydrogen) (12.1 g, 33.9 mmol, 98%) as a yellowish solid (99.5% purity, according to Method C).

Example 4

R)-2-(2-Amino-5-fluorophenyl)-4-cyclopropyl-1,1,1-trifluorobut-3-yn-2-ol methanesulfonate (2:3 mol/mol (1S,2R)-PNE (18.2%-w/w, 20.3 g, 18.0 mmol) in THF/toluene (9:1-w/w) was charged under nitrogen to a dry, jacketed 150 mL-reactor with agitator. Diethylzinc in toluene (29.9%-w/w, 6.20 g, 15.0 mmol) was added by syringe while keeping the temperature at 17 to 22° C. Then the mixture was aged for 30 min at 17° C. Cyclopropylacetylene in toluene (69.6%-w/w, 6.82 g, 71.8 mmol) was added at 17° C. and the reaction mixture was aged for 60 min at 20° C. To the reaction mixture BuLi in toluene (19.3 g, 3.06 mol/kg, 59.1 mmol) and 1-(2-amino-5-fluorophenyl)-2,2,2-trifluoroethanone (CAS [214288-07-0], CN46221, compound of formula IV, wherein $R^1$ is trifluoromethyl, $R^8$ is 5-fluoro, $R^9$ is hydrogen and $R^{10}$ is hydrogen) (36.9%-w/w, 33.7 g, 60.0 mmol) in THF/toluene (1:1-w/w) were added in parallel over a period of 3 h at 20° C. The addition of BuLi was kept 10 min in advance of the CN46221 addition. After completed addition the reaction mixture was stirred at 20° C. for 30 min, heated over a period of 60 min to 30° C. and aged for 6 h at 30° C. The reaction mixture was stirred overnight at 0° C. HPLC indicated 82.4% conversion and 96.0% ep of (R)-2-(2-amino-5-fluorophenyl)-4-cyclopropyl-1,1,1-trifluorobut-3-yn-2-ol (CN46619) according to Method B. The reaction mixture was diluted with toluene (27.6 g) and quenched by adding aqueous citric acid (1 M, 45.3 g). The phases were separated and the aqueous phase was discarded. The organic phase was successively washed with water (9.1 g), aqueous NaHCO₃ (5%-w/w, 24.2 g) and water (12.0 g). The organic phase was alternating concentrated and diluted with toluene to remove THF. The obtained residue (51.0 g) was diluted with isopropyl alcohol (16.7 g) and toluene (60.0 g). Methanesulfonic acid (8.36 g, 87.0 mmol) was added by a syringe pump over a period of 75 min at 30° C. The mixture was aged and cooled stepwise over 2 h 10 min to reach 5° C. before the mixture was filtered. The filter cake was washed with toluene/isopropyl alcohol (10:1-w/w, 27.0 g) and dried under reduced pressure at 40° C. The dry product (R)-2-(2-amino-5-fluorophenyl)-4-cyclopropyl-1,1,1-trifluorobut-3-yn-2-ol methanesulfonate (2:3 mol/mol, CN46619-MSA, compound of formula II, wherein $R^1$ is trifluoromethyl, $R^2$ is cyclopropyl, $R^8$ is 5-fluoro, $R^9$ is hydrogen and $R^{10}$ is hydrogen) (19.46 g, 46.6 mmol, 78% yield) was obtained as a yellowish solid (99.8%-w/w by ¹H-NMR, and 99.8% ep, according to Method B).

Example 5

(R)-4-(Cyclopropylethynyl)-6-fluoro-4-(trifluoromethyl)-1,4-dihydro-2H-3,1-benzoxazin-2-one (R)-2-(2-Amino-5-fluorophenyl)-4-cyclopropyl-1,1,1-trifluorobut-3-yn-2-ol methanesulfonate (CN46619-MSA) of example 4 (14.0 g, 33.5 mmol) in ethyl acetate/heptanes (40 g, 6/4 v/v) was charged to a jacketed 150 mL-reactor with agitator and off-gas scrubber with caustic soda. After addition of aqueous Na₂CO₃ (12%-w/w, 26.9 g, 30.3 mmol) the mixture was stirred for 5 min at 15° C. The aqueous phase was separated and discarded. Aqueous Na₂CO₃ (12%-w/w, 34.1 g, 38.4 mmol) was charged to the organic phase, then triphosgene (3.73 g, 12.6 mmol) was added in portions over a period of 25 min at 10° C. The reaction mixture was stirred for 2 h at 8° C. The mixture was charged with heptanes (15.9 g), the phases were separated and the aqueous phase discarded. The organic phase was washed with water (12 mL), dried over MgSO₄, filtered and concentrated to dryness. After drying under vacuum at 50° C., the product (R)-4-(cyclopropylethynyl)-6-fluoro-4-(trifluoromethyl)-1,4-dihydro-2H-3,1-benzoxazin-2-one (CN46686, compound of formula I, wherein $R^1$ is trifluoromethyl, $R^2$ is cyclopropyl, $R^8$ is 6-fluoro, $R^9$ is hydrogen and $R^{10}$ is hydrogen 9.78 g, 32.7 mmol, 97%) was obtained as a yellowish solid (99.4% purity, according to Method C).

Example 6

Cyclisation of SD573 with Diphosgene

Aqueous Na₂CO₃ (12%-w/w, 183 g, 0.206 mol) was charged to SD573-MSA ((S)-2-(2-amino-5-chlorophenyl)-4-cyclopropyl-1,1,1-trifluorobut-3-yn-2-ol mesylate (2:3 mol/mol)=methanesulfonate of the S-enantiomer of the compound of formula II, wherein $R^1$ is trifluoromethyl, $R^2$ is cyclopropyl, $R^8$ is 5-chloro, $R^9$ is hydrogen and $R^{10}$ is hydrogen; 100 g, 0.23 mol, corresponding to 66.8 g of SD573 free base, 99.6% ee, prepared accordingly to Example 1) in ethyl acetate/heptanes (203 g, 1.5:1 v/v). The mixture was stirred for 5 min at 15° C. Hydrolysis of the mesylate ended at about pH 9.0 of the aqueous phase. Then a phase separation was performed and the aqueous phase was removed. Aqueous Na₂CO₃ (12%-w/w, 232 g, 0.262 mol) was charged to the organic phase. To the biphasic mixture, liquid diphosgene (24 g, 120 mmol) was added in 90 min at 12° C. After a conversion of more than 99.7% was reached, according to Method C, heptanes (204 g) were charged. The reaction mixture was then heated to 20° C., the aqueous phase was separated and discarded, while the organic phase was washed with water (about 80 g). The organic layer was heated under reduced pressure, ethyl acetate distilled off and heptanes were charged to the reaction mixture to achieve a residual ethyl acetate content of 5.5%-w/w and a ratio of heptanes to organic matter of 10 L/kg in view of originally added SD573-MSA. Then the mixture was heated to dissolve all organic matter. The solution was seeded with 0.8 g of DMP-266 (DMP-266=S-enantiomer of the compound of formula I, wherein $R^1$ is trifluoromethyl, $R^2$ is cyclopropyl, $R^8$ is 6-chloro, $R^9$ is hydrogen and $R^{10}$ is hydrogen) at 55° C. and stirred for about 15 min at 55° C. The mixture was then cooled to 50° C. and hold for 120 min. Then the mixture was further cooled within 2 h from 50° C. to 25° C. and within another 2 h ramp to about −10° C. Finally, the mixture was stirred for about 1 h at −10° C. maximum and then filtered. The filter cake (wet product) was washed with pre-cooled heptanes (2×50 mL) at 0° C. maximum. The solid was dried in vacuo to yield 94.2% (68.4 g, 216 mmol) of DMP-266 at a purity of 99.9%-w/w according to Method D. The sample comprises 99.8%-w/w S-enantiomer, i.e. an enantiomeric excess (ee) of 99.6%.

Example 7

Cyclisation of SD573 with Diphosgene

Aqueous Na₂CO₃ (12%-w/w 91.5 g, 0.103 mol) was charged to SD573-MSA (50 g, 0.115 mol, corresponding to 33.4 g of SD573 free base, 99.6% ee, prepared accordingly to Example 1) in ethyl acetate/heptanes (101.5 g, 1.5/1 v/v). The mixture was stirred for 5 min at 15° C. Hydrolysis of the mesylate ended at pH 6.4 in the aqueous phase. A phase separation was performed and the aqueous phase was removed. The remaining organic phase was cooled to 12° C. and aqueous Na₂CO₃ (12%-w/w, 106 g, 0.12 mol) was charged. To the biphasic mixture, liquid diphosgene (11.4 g, 57 mmol) was added in 90 min at 12° C. After a total conversion was reached according to Method C, heptanes (68.8 g) was charged. The reaction mixture was then heated to 20° C., stirred 30 min and the aqueous phase was removed. The organic phase was heated under reduced pressure, ethyl acetate was distilled off and heptanes charged to the reaction mixture to achieve a residual ethyl acetate content of 4.4 w % and a ratio of heptanes to organic matter of 6.5 L/kg in view of originally added SD573-MSA. Then the obtained mixture was heated to dissolve all organic matter. The solution was seeded with DMP-266 (0.4 g) at 55° C. and stirred for about 15 min at 55° C. The mixture was then cooled to 50° C. and hold for 120 min. The mixture was further cooled in 2 h from 50° C. to 25° C. and within another 2 h to −10° C. maximum. The mixture finally was stirred for about 1 h at −13° C. and then filtered. The filter cake (wet product) was washed with pre-cooled heptanes (2×50 mL) at 0° C. maximum. The solid was dried in vacuo to yield 92.1% (33.45 g, 105 mmol) of DMP-266 of a purity of 99.9%-w/w according to Method D. The sample comprises 99.8%-w/w S enantiomer, i.e. 99.6% ee.

Example 8

Cyclisation of SD573 with Triphosgene

SD573-MSA (50 g, 0.114 mol, corresponding to 33.4 g of SD573 free base, 99.6% ee, prepared accordingly to Example 1) was dissolved in an ethyl acetate/heptanes mixture (164 g, 1:1 v/v) and charged with aqueous $Na_2CO_3$ (12%-w/w, 91.5 g, 0.104 mol). After hydrolysis of the mesylate a pH of about 7.0 was measured in the aqueous phase. The mixture was stirred for at least 5 min at 15° C. Then a phase separation was performed and the aqueous phase was removed. The mixture was cooled below 12° C. and aqueous $Na_2CO_3$ (12%-w/w, 116 g, 0.131 mol) was charged. To the biphasic mixture, triphosgene (12.5 g, 42 mmol) was added at 10° C. maximum in five portions within 90 min. The mixture was stirred further 15 min below 15° C. After a total conversion was reached according to Method C, heptanes (54 g) was charged. The reaction mixture was then heated to 20° C. and the aqueous phase was removed. The organic phase was washed with water (40 g) and then heated under reduced pressure, ethyl acetate distilled off and heptanes charged to the reaction mixture to achieve a residual ethyl acetate content of 4.6%-w/w and a ratio of heptanes to organic matter of 6.5 L/kg in view of originally added SD573-MSA. The solution was seeded with DMP 266 (0.4 g) at 57° C. and stepwise cooled under stirring at −10° C. within 2 h 15 min. The mixture was stirred at −10° C. maximum overnight and then filtered. The filter cake was washed with pre-cooled heptanes (2×25 mL) at 0° C. maximum. The solid was dried in vacuo to yield 95% of DMP-266 (34.22 g, 108 mmol) at a purity of 100%-w/w, according to Method D. The sample comprises 99.8%-w/w S-enantiomer, i.e. 99.6% ee.

Example 9

Cyclisation of SD573 with Triphosgene

SD573-MSA (100 g, 0.23 mol, corresponding to 66.8 g of SD573 free base, 99.6% ee, prepared accordingly to Example 1) was dissolved in ethyl acetate/heptanes (203 g, 1.5:1 v/v) and charged with aqueous $Na_2CO_3$ (12%-w/w, 183 g, 0.207 mol) at about 15° C. A pH of 7 to 9 was reached in the aqueous phase. The mixture was stirred for 5 min at 15° C. Then the phase separation was performed and the aqueous phase was removed. The mixture was cooled below 12° C. and aqueous $Na_2CO_3$ (12%-w/w, 232 g, 0.263 mol) was charged. To the biphasic mixture, triphosgene (24.08 g, 81 mmol) was added in 10 portions within 120 min at less than 12° C. The mixture was stirred further 10 min at about 12° C. After a total conversion was reached according to Method C, heptanes (204 g) were charged. The reaction mixture was then heated to 20° C. and the aqueous phase was removed. The organic phase was washed with water (80 g) and then heated under reduced pressure to partially remove ethyl acetate, while heptanes were charged to the reaction mixture to achieve a residual ethyl acetate content of 5.8%-w/w and a ratio of heptanes to organic matter of 7.0 L/kg in view of originally added SD573-MSA. The solution was seeded with DMP-266 (0.8 g) at 55° C. and stirred for 15 min. Then the mixture was cooled to 50° C. within 20 min, hold for 2 h, cooled to 25° C. within 2 h, cooled to about −10° C. within 2 h. After cooling to about −10° C. and stirring overnight the mixture was filtered. The isolated product was washed with pre-cooled heptanes (2×50 mL) at −10° C. maximum. The solid was dried in vacuo to yield 85.4% DMP-266 (62 g, 19.6 mmol) at a purity of 100%-w/w, according to Method D. The sample comprises 99.8%-w/w S-enantiomer, i.e. 99.6% ee.

Example 10

Cyclisation of SD573 with Triphosgene

Aqueous $Na_2CO_3$ (14%-w/w, 135 g, 0.178 mol) was charged to SD573 free base (33.4 g, 0.115 mol) in ethyl acetate/heptanes (70.4 g of 45:55 v/v) at 15° C. The mixture was cooled to 8° C. and triphosgene in heptanes (26.8%-w/w, 112 g, 101 mmol) was added within 60 min, while the temperature was kept at 5° C. to 12° C. After 60 min a total conversion was reached, according to Method C. The reaction mixture was heated to 25° C. Then a phase separation was performed and the aqueous phase was removed. The organic phase was heated under reduced pressure, ethyl acetate partly was distilled off and heptanes were charged to the reaction mixture to achieve a residual ethyl acetate content of about 2.5%-w/w and a ratio of heptanes to organic matter of about 15 L/kg in view of originally added SD573 free base. Then the mixture was heated to dissolve all organic matter and afterwards seeded with DMP-266 (overall 1.4 g) at 55° C. No product crystallized and therefore the organic phase was heated under reduced pressure to partially remove ethyl acetate, while heptanes were charged to the reaction mixture to achieve a residual ethyl acetate content of less then 3% (w/w) and a ratio of heptanes to organic matter of about 15 L/kg in view of originally added SD573 free base. Then the mixture was heated to dissolve all organic matter and afterwards seeded with DMP-266 (1.5 g) at 51° C. and stirred for about 140 h at 51° C. The slurry was stepwise cooled under stirring within 4 h to reach −15° C. The slurry was stirred for 16 h at −15° C. and then filtered. The isolated product was washed with pre-cooled heptanes (2×55 mL) at −10° C. maximum. The solid was dried in vacuo to yield 92.9% (33.7 g, 107 mmol) of DMP-266, at a purity of 99.6%-w/w, according to Method D. The sample comprises 99.8%-w/w S-enantiomer, i.e. 99.6% ee.

Example 11

Cyclisation of SD573 with Triphosgene

Aqueous $Na_2CO_3$ (12%-w/w, 91.5 g, 0.103 mol) was charged to SD573-MSA (50 g, 0.115 mol, corresponding to 33.4 g of SD573 free base, prepared accordingly to Example 1) in ethyl acetate/heptanes (90.8 g, 55/45 v/v). The mixture was stirred for 5 min at 15° C. resulting in a pH of 6.8 of the aqueous phase. Then a phase separation was performed and the aqueous phase was removed. The organic phase was heated under reduced pressure and the solvent was partially removed (32.3 g, 41 mL) to obtain a ratio of SD573 free base to solvent of about 1:1.75 (w/w). The distillate contained about 53.2 w % of ethyl acetate. The mixture comprising the SD573 free base was cooled to 12° C. and aqueous $Na_2CO_3$ (12%-w/w, 96 g, 0.109 mol) was charged. To the biphasic mixture, triphosgene in ethyl acetate (31%-w/w, 32.7 g, 34 mmol) was added in 66 min at 7 to 12° C. The mixture was stirred 15 min at 12° C. maximum. After a conversion of 90.2% was reached, according to Method C, additional heptanes (86 g) were charged and the reaction mixture was heated to 20° C. Then a phase separation was performed and the aqueous phase was removed. The organic phase was heated under reduced pressure to partially remove ethyl acetate while heptanes were charged to the organic phase to achieve a residual ethyl acetate content of 6.8%-w/w (target 3 to 7%-w/w) and a ratio of heptanes to organic matter of 6.8 L/kg in view of originally added SD573-MSA. The solution was seeded with DMP-266 (0.4 g) at 47° C. and stirred for 150 min at 47 to 55° C. Then the mixture was slowly cooled to −10° C. and filtered. The filter cake was washed with pre-cooled heptanes (2×25 mL) at −10° C. maximum. The solid was dried in vacuo to yield 81.1% (29.46 g, 0.093 mmol) of DMP-266 of a purity of 97.2%-w/w according to Method D.

Example 12

Cyclisation of SD573 with Triphosgene

Aqueous $Na_2CO_3$ (12%-w/w, 275.1 g, 0.311 mol) was charged to SD573-MSA (150 g, 0.345 mol, corresponding to 100.2 g of SD573 free base, prepared accordingly to Example 1) in ethyl acetate/heptanes (272.1 g, 55/45 v/v). After stirring the mixture for 5 min at 15° C. a pH of 7.7 was measured. Then a phase separation was performed and the aqueous phase was discarded. The organic phase (ethyl acetate/heptanes ratio of 61.5/38.5 w/w) was split into 3 parts each comprising about 33 g of SD573 free base. With an aim to test the stability of SD573 free base in ethyl acetate/heptanes mixtures, the $1^{st}$ part was stored for 4 days at 4° C. before performing Example 12.1, the $2^{nd}$ part was stored for 7 days at 4° C. before performing Example 12.2, and the $3^{rd}$ part was stored for 10 days at 4° C. before performing Example 12.3.

Example 12.1

The $1^{st}$ part of the organic phase of Example 12 (123.5 g) was heated under reduced pressure to partially remove the solvent until the distillate contained 60 w % of ethyl acetate (about 33 g). The remaining mixture was cooled to 12° C. and aqueous $Na_2CO_3$ (12%-w/w, 117 g, 0.132 mol) was charged. To the biphasic mixture, triphosgene in ethyl acetate (36%-w/w, 35 g, 42 mmol) was added in 60 min at less than 12° C. The mixture was stirred 15 min at less than 12° C. After a total conversion was reached according to Method C, heptanes (86 g) were charged and the reaction mixture was heated to 20° C. Then a phase separation was performed and the aqueous phase was removed. The organic phase was washed with water (40 g). The organic phase was heated under reduced pressure to party remove ethyl acetate, while heptanes were charged to the reaction mixture to achieve a residual ethyl acetate content of 5.5%-w/w (target 3 to 7%-w/w). A ratio of heptanes to organic matter of 6.3 L/kg in view of originally added SD573-MSA was obtained for crystallisation. The solution was seeded with DMP-266 (0.4 g) at 57° C. and stirred for 15 min at the seeding temperature. The mixture was stepwise cooled under stirring to −15° C. within 6 h 20 min, stirred overnight at −10° C. and finally filtered. The filter cake was washed with pre-cooled heptanes (2×25 mL) at −10° C. maximum. The solid was dried in vacuo to yield 89.4% (32.17 g, 102 mmol) of DMP-266 at a purity of 100%-w/w according to Method D.

Example 12.2

The $2^{nd}$ part of the organic phase of Example 12 (122.0 g) was heated under reduced pressure to partially remove the solvent until the distillate contained 53 w % of ethyl acetate (about 31 g). The mixture was cooled to 12° C. and aqueous $Na_2CO_3$ (12%-w/w, 117 g, 0.132 mol) was charged. To the biphasic mixture triphosgene in ethyl acetate (36%-w/w, 35 g, 42 mmol) was added in 60 min at 12° C. maximum. The mixture was stirred for 15 min at 12° C. maximum. A total conversion was obtained according to Method C. Heptanes (86 g) were charged and the reaction mixture was heated to 20° C. Then a phase separation was performed and the aqueous phase was removed. The organic phase was washed with water (40 g) and then heated under reduced pressure to partially remove ethyl acetate, while heptanes were charged to the reaction mixture to achieve a residual ethyl acetate content of 5.7%-w/w (target 3 to 7%-w/w). A ratio of heptanes to organic matter of 6.4 L/kg in view of originally added SD573-MSA was obtained for crystallisation. The mixture was seeded with DMP-266 (0.4 g) at 57° C. and stepwise cooled under stirring within 6 h to reach −15° C. Then the mixture was stirred at −10° C. overnight and filtered. The filter cake was washed with pre-cooled heptanes (2×50 mL) at −10° C. maximum. The solid was dried in vacuo to yield 89.5% (32.21 g, 102 mmol) of DMP-266 at a purity of 100%-w/w according to Method D.

Example 12.3

The $3^{rd}$ part of the organic phase of Example 12 (122.5 g) was heated under reduced pressure to partially remove the solvent until the distillate contained 53.6 w % of ethyl acetate (about 32.3 g). The mixture was cooled to 9° C. before aqueous $Na_2CO_3$ (12%-w/w, 117 g, 0.132 mol) was charged. To the biphasic mixture triphosgene in ethyl acetate (36%-w/w, 35 g, 42 mmol) was added in 60 min at 12° C. maximum and the mixture stirred for 1 h at 12° C. maximum. A total conversion was obtained according to Method C. Heptanes (86 g) were charged and the reaction mixture was heated to 20° C. A phase separation was performed and the aqueous phase was removed. The organic phase was washed with water (40 g) and then heated under reduced pressure to partially remove ethyl acetate, while heptanes were charged to the reaction mixture to achieve a residual ethyl acetate content of 5.8%-w/w. A ratio of heptanes to organic matter of 6.2 L/kg in view of originally added SD573-MSA was obtained for crystallisation. The mixture was seeded with DMP-266 (0.4 g) at 57° C. and stepwise cooled under stirring to −15° C. within 6 h. The mixture was stirred at −10° C. overnight and then filtered. The filter cake was washed with pre-cooled heptanes (2×25 mL) at −10° C. maximum. The solid was dried in vacuo to yield 90% of DMP-266 (32.4 g, 103 mmol) at a purity of 100%-w/w according to Method D.

Example 13

Cyclisation of SD573 with Triphosgene

Aqueous $Na_2CO_3$ (14%-w/w, 160 g, 0.211 mol) was charged to SD573-MSA (100 g, 0.229 mol, corresponding to 66.8 g of SD573 free base, prepared accordingly to Example 1) in ethyl acetate/heptanes (158.8 g 1/1 v/v). The mixture was stirred at approx. 15° C. resulting in a pH of 6.8 of the aqueous phase. Then a phase separation was performed and the aqueous phase was removed. The organic phase was cooled to 12° C. and aqueous $Na_2CO_3$ (14%-w/w, 214 g, 0.283 mol) was charged. To the biphasic mixture triphosgene in ethyl acetate (35.7%-w/w, 67.2 g, 81 mmol) was added in 60 min at 12° C. maximum. The mixture was stirred for 30 min at 12° C. maximum. Heptanes (96 g) were charged and a total conversion was obtained according to Method C. The reaction mixture was heated to 20° C. Then a phase separation was performed and the aqueous phase was removed. Aqueous $Na_2CO_3$ (14%-w/w, 92 g, 0.121 mol) was added to the organic phase and stirred for 25 min at 20° C. Then a phase separation was performed and the aqueous phase was removed. The organic phase (360 g) was split into two parts.

Example 13.1

The $1^{st}$ part of the organic phase of Example 8 (180 g) was washed with water (80 g), phase separation was performed and the aqueous phase was removed. Then the organic phase was heated under reduced pressure, ethyl acetate partially distilled off and heptanes charged to the reaction mixture to achieve a residual ethyl acetate content of 3%-w/w (target 3 to 7%-w/w) was obtained. Finally total 10 L/kg SD573-MSA heptanes was achieved for the crystallisation. The solution was seeded with DMP-266 (0.2 g) at 55° C. and stepwise cooled under stirring to −15° C. within 7 h. The mixture was stirred at −15° C. overnight and then filtered. The filter cake was washed with pre-cooled heptanes (2×50 mL) at −10° C. maximum. The solid was dried in vacuo to yield 93% (33.47 g, 105 mmol) of DMP-266, the purity is 98.8%-w/w, according to Method D.

Example 13.2

The $2^{nd}$ part of the organic phase of Example 8 (180 g) was heated under reduced pressure to partially remove ethyl acetate, while heptanes were charged to the reaction mixture, to achieve a residual ethyl acetate content of 3.4%-w/w (target 3 to 7%-w/w). A ratio of heptanes to organic matter of 10 L/kg in view of originally added SD573-MSA was obtained for crystallisation. The mixture was seeded with 0.2 g of DMP-266 at 55° C. and stepwise cooled under stirring within 6 h 40 min to reach −15° C. The mixture was stirred at −10° C. overnight and then filtered. The filter cake was washed with pre-cooled heptanes (2×50 mL) at −10° C. maximum. The solid was dried in vacuo to yield 96% (34.87 g, 110 mmol) of DMP-266 at a purity of 97.7%-w/w according to Method D.

Example 14

Cyclisation of SD573 with Triphosgene

Aqueous $Na_2CO_3$ (14%-w/w, 80 g, 0.106 mol) was charged to SD573-MSA (50 g, 0.115 mol, corresponding to 33.4 g of SD573 free base, prepared accordingly to Example 1) in of ethyl acetate/heptanes (79.4 g, 1/1 v/v) and charged. After stirring for 15 min a pH of 6.4 was measured in the aqueous phase. The mixture was stirred for 5 min at 15° C. Then a phase separation was performed and the aqueous phase was removed. The mixture was cooled to 12° C. and aqueous $Na_2CO_3$ (14%-w/w, 107 g, 0.141 mol) was charged. Triphosgene in ethyl acetate (35.7%-w/w, 33.6 g, 40.5 mmol) was added to the biphasic mixture for 60 min at 12° C. maximum. The mixture was stirred 30 min at 12° C. maximum. Heptanes (48 g) were charged and a total conversion was obtained according Method C. The reaction mixture was heated to 20° C. Then a phase separation was performed and the aqueous phase was removed. The organic phase was washed with water (80 g) and then heated under reduced pressure, to partially remove ethyl acetate, while heptanes were charged to the reaction mixture, to achieve a residual ethyl acetate content of 3.2%-w/w. A ratio of heptanes to organic matter of 9.6 L/kg in view of originally added SD573-MSA was obtained for crystallisation. The mixture was seeded with 0.2 g of DMP-266 at 55° C., and stepwise cooled under stirring within 7 h to reach −15° C. The mixture was stirred at −15° C. overnight and then filtered. The filter cake was washed with pre-cooled heptanes (50 mL) at −10° C. maximum. The solid was dried in vacuo to yield 97% (34.49 g, 110 mmol) of DMP-266 at a purity of 96.5%-w/w according to Method D.

Example 15

Cyclisation of SD573 with Triphosgene

Aqueous $Na_2CO_3$ (14%-w/w, 80 g, 0.106 mol) was charged to SD573-MSA (50 g, 0.114 mol, corresponding to 33.4 g of SD573 free base, prepared accordingly to Example 1) in ethyl acetate/heptanes (79.4 g, 1/1 v/v). After stirring for 15 min a pH of 6.1 was measured in the aqueous phase. The mixture was stirred for 5 min at 15° C. Then the phase separation was performed and the aqueous phase was removed. The mixture was cooled to 12° C. and aqueous $Na_2CO_3$ (14% w/w, 135 g, 0.178 mol) was charged. To the biphasic mixture triphosgene in ethyl acetate (35.7%-w/w, 33.6 g, 40.5 mmol) was added in 60 min at 12° C. maximum. The mixture was stirred 30 min at 12° C. maximum. Heptanes (48 g) were charged and a total conversion was obtained according to Method C. The reaction mixture was heated to 20° C. Then a phase separation was performed and the aqueous phase was removed. The organic phase was washed with water (80 g) and then heated under reduced pressure to partially remove ethyl acetate, while heptanes were charged to the reaction mixture, to achieve a residual ethyl acetate content of 2.8%-w/w. A ratio of heptanes to organic matter of 9.5 L/kg in view of originally added SD573-MSA was obtained for crystallisation. The solution was seeded with DMP-266 (0.2 g) at 55° C. and stepwise cooled under stirring within 4 h 35 min to reach to −15° C. The mixture was stirred overnight at −15° C. and then filtered. The filter cake was washed with pre-cooled heptanes (2×50 mL) at −10° C. maximum. The solid was dried in vacuo to yield 97.6% of DMP-266 (35.12 g, 111 mmol) at a purity of 95.1%-w/w according to Method D.

Example 16

Cyclisation of SD573 with Phosgene

Aqueous $Na_2CO_3$ (12%-w/w, 183 g, 0.207 mol) was charged to SD573-MSA (100 g, 0.228 mol, corresponding to 66.8 g of SD573 free base, prepared accordingly to Example 1) in ethyl acetate/heptanes (203 g, 1.5:1 v/v). After stirring for 15 min a pH of 7.2 was measured in the aqueous phase. The mixture was stirred for 5 min at 15° C. Then the phase separation was performed and the aqueous phase was removed. The mixture was cooled to 12° C. and aqueous $Na_2CO_3$ (12%-w/w, 232 g, 0.263 mol) was charged. Phosgene (24.8 g, 251 mmol) was added to the biphasic mixture in 90 min at 12° C. maximum. Heptanes (136 g) were charged to the mixture and a total conversion was obtained according to Method C. The reaction mixture was heated to 20° C. Then a phase separation was performed and the aqueous phase was removed. The organic phase was washed with water (80 g) and then heated under reduced pressure to partially remove ethyl acetate, while heptanes were charged to the reaction mixture, to achieve a residual ethyl acetate content of less then 7%-w/w. A ratio of heptanes to organic matter of 9.7 L/kg in view of originally added SD573-MSA was obtained for crystallisation. The solution was seeded with DMP-266 (0.8 g) at 55° C., stepwise cooled under stirring within 6 h 15 min to reach −15° C. and then filtered. The filter cake was washed with pre-cooled heptanes (2×50 mL) at 0° C. maximum. The solid was dried in vacuo to yield 95.7% of DMP-266 (68.91 g, 218 mmol) at a purity of 100%-w/w according to Method D.

Example 17

Cyclisation of SD573 with Phosgene

SD573-MSA (50 g, 0.114 mol, corresponding to 33.4 g of SD573 free base, prepared accordingly to Example 1) was dissolved in ethyl acetate/heptanes (102 g, 55:45 v/v) and charged with aqueous $Na_2CO_3$ (12%-w/w, 91 g, 0.103 mol). After stirring for 15 min a pH of about 7 was measured in the aqueous phase. The mixture was stirred for 5 min at 15° C. Then the phase separation was performed and the aqueous phase was separated and discarded. The organic phase was cooled to 12° C. and charged with aqueous $Na_2CO_3$ (12%-w/w, 157 g, 0.178 mol). To the biphasic mixture phosgene (16.9 g, 171 mmol) was added in 130 min at 12° C. maximum. Heptanes (43 g) were charged and a total conversion was obtained according to Method C. The reaction mixture was heated to 20° C. Then a phase separation was performed and the aqueous phase was removed. The organic phase was washed with water (80 g) and then heated under reduced pressure to partially remove ethyl acetate, while heptanes were charged to the reaction mixture, to achieve a residual ethyl acetate content of 3.5%-w/w. A ratio of heptanes to organic matter of ca. 10 L/kg in view of originally added SD573-MSA was obtained for crystallisation. The solution was seeded with DMP-266 (0.4 g) at 62° C. and stepwise cooled under stirring to −5° C. overnight and then filtered. The filter cake was washed with pre-cooled heptanes (2×50 mL) at 0° C. maximum. The solid was dried in vacuo to yield 93% of DMP-266 (33.86 g, 107 mmol) at a purity of 98.5%-w/w according to Method D.

Example 18

(S)-2-(2-Amino-5-methylphenyl)-4-cyclopropyl-1,1,1-trifluorobut-3-yn-2-ol

A solution of (1R,2S)-PNE (17.6%-w/w, 21.0 g, 18.0 mmol) in a THF/toluene mixture (9:1-w/w) was charged in a vessel at room temperature. A solution of diethylzinc in toluene (29.9%-w/w, 6.10 g, 14.8 mmol) was added at 17 to 25° C. and the mixture was aged at said temperature range for 30 min. A solution of cyclopropylacetylene (compound of formula III, wherein $R^2$ is cyclopropyl) in toluene (69.6%-w/w, 8.55 g, 90.0 mmol) was added at 18° C. and the resulting mixture was aged at 20° C. for 60 min. A solution of BuLi in toluene (3.09 mol/kg, 17.6 g, 54.4 mmol) and a solution of 1-(2-amino-5-methylphenyl)-2,2,2-trifluoroethanone (CN46217, compound of formula IV, wherein $R^1$ is trifluoromethyl, $R^8$ is 5-methyl, $R^9$ is hydrogen and $R^{10}$ is hydrogen) (36.5%-w/w, 33.4 g, 60.0 mmol) in toluene/THF (1:1-w/w) were added in parallel to the reaction mixture at 20° C. within 3 h. The addition of BuLi was started 10 min in advance of the CN46217 addition. After completed addition of CN46217 the reaction mixture was stirred for 30 min at 20° C., then heated to 30° C. over a period of 60 min and aged for 6 h at 30° C. The reaction mixture was stirred at 0° C. overnight. HPLC (Method B) indicated 72.3% conversion and 96.7% enantiomeric purity. The reaction mixture was diluted with toluene (25.8 g) and quenched by addition of aqueous citric acid (1 M, 73.9 g). After stirring for 15 min the phases were separated and the aqueous phase was discarded. The organic phase was successively washed with water (9.1 g), aqueous $NaHCO_3$ solution (5%-w/w, 24.0 g), and water (12.0 g). The organic phase was partially concentrated (60 g residual solution), diluted with toluene (30 g), and partially concentrated again (52 g residue). The residue was diluted with toluene (65 g), cooled to 5° C. and aged over night. The crystals were filtered, washed with cold (approx. 5° C.) toluene (10 g) and dried under vacuum at 40° C. The wet product (10.8 g) obtained as off-white solid with a purity of 99.2 and 100% ep according to method B. The crude product was purified by slurring it in a mixture of toluene (10 mL) and heptane (40 mL) at room temperature for 1 h, filtered and dried at 40° C. in vacuo. The product (compound of formula II, wherein $R^1$ is trifluoromethyl, $R^2$ is cyclopropyl, $R^8$ is 5-methyl, $R^9$ is hydrogen and $R^{10}$ is hydrogen) was obtained as white solid (10.6 g, 38 mmol, 64% yield) with a purity of 99.4% and 100% ep according to method B. The assay was 97.0%-w/w according to $^1$H-NMR.

Example 19

(S)-4-(Cyclopropylethynyl)-6-methyl-4-(trifluoromethyl)-1,4-dihydro-2H-3,1-benzoxazin-2-one (2S)-2-(2-Amino-5-methylphenyl)-4-cyclopropyl-1,1,1-trifluorobut-3-yn-2-ol (CN46624) obtained according example 18 (97.0%-w/w, 10.0 g, 36.0 mmol) in ethyl acetate/heptanes (2:1-w/w, 30 g) was charged to a jacketed 150 mL-reactor with agitator and off-gas scrubber with caustic soda. The reaction mixture was cooled to 7° C. and aqueous $Na_2CO_3$ solution (12%-w/w, 33.5 g) was added. Triphosgene (3.67 g, 12.4 mmol) was added in portions over a period of 25 min at 7 to 15° C. The reaction mixture was stirred for 15 min at 8° C. and sampled for conversion control (99.8% conversion according to method C). The precipitated solid was dissolved by adding ethyl acetate (25 g) and the phases were separated. The organic phase was washed with water (10 g), dried over $MgSO_4$, filtered and concentrated under vacuum to dryness. The crude product (11.6 g) was obtained as a white solid (purity 96.9% according to HPLC method C). Hexane (20 mL) was added ct and the mixture was stirred for 1 h at room temperature. The product was filtered, washed with cold hexane (10 mL) and dried at 35° C. under vacuum. The product (compound of formula I, wherein $R^1$ is trifluoromethyl, $R^2$ is cyclopropyl, $R^8$ is 6-methyl, $R^9$ is hydrogen and $R^{10}$ is hydrogen) was obtained as white solid (9.76 g, 32.9 mmol, 91% yield) with a purity of 98.8% according to method C and an assay of 99.6% w-/w according to $^1$H-NMR.

Example 20

2-(2-Amino-5-chlorophenyl)-1,1,1-trifluorooct-3-yn-2-ol methanesulfonate (2:3 mol/mol)

Example 20.1

R)-2-(2-Amino-5-chlorophenyl)-1,1,1-trifluorooct-3-yn-2-ol methanesulfonate (2:3 mol/mol A solution of (1S,2R)-PNE (18.7%-w/w, 19.7 g, 18.0 mmol) in THF/toluene (9:1-w/w) was charged to a vessel at room temperature. A solution of diethylzinc in toluene (29.9%-w/w, 6.10 g, 14.8 mmol) was added at 17 to 25° C. and the mixture was aged at said temperature for 30 min, 1-hexyne (97%-w/w, 6.10 g, 72.0 mmol, compound of formula III, wherein $R^2$ is n-butyl) was added at 18° C. and the resulting solution was aged at 20° C. for 60 min. A solution of BuLi in toluene (3.09 mol/kg, 17.8 g, 55.0 mmol) and a solution of 1-(2-amino-5-chlorophenyl)-2,2,2-trifluoroethanone (CN23315, a compound of formula IV, wherein $R^1$ is trifluoromethyl, $R^8$ is 5-chloro, $R^9$ is hydrogen and $R^{10}$ is hydrogen) in toluene/THF (1:1 w/w) (39.6%-w/w, 33.8 g, 60.0 mmol) were added in parallel to the reaction mixture at 20° C. within 3 h. The addition of BuLi was started 10 min in advance of the CN23315 addition. After completed addition of CN23315 the reaction mixture was stirred for 30 min at 20° C., then heated to 30° C. over a period of 60 min and aged for 6 h at 30° C. The reaction mixture was stirred at 0° C. overnight. HPLC (Method B) indicated 89.6% conversion. The reaction mixture was diluted with toluene (25.8 g) and quenched by addition of aqueous citric acid solution (1 M, 44.1 g). After stirring for 15 min the phases were separated and the organic phase successively washed with water (9.1 g), aqueous NaHCO$_3$ solution (5%-w/w, 24.0 g) and water (12.0 g). The organic phase was partially concentrated (51 g residual solution), diluted with toluene (30 g), and partially concentrated again (58 g residue). The residue was diluted with toluene (59 g) and isopropyl alcohol (1.50 g). Methanesulfonic acid (10.48 g, 114 mmol) was added at 30° C. over a period of 30 min and the mixture was stirred for 30 min. A second portion methanesulfonic acid (2.89 g, 30 mmol) was added at 30° C. over a period of 30 min. The mixture was stirred at 30° C. for 30 min, cooled to 5° C. over a period of 60 min, and aged at 5° C. for 30 min. The crystals were filtered, washed with cold toluene (10 g) and dried under vacuum at 40° C. The crude product (19.3 g) was obtained as yellowish solid with a purity of 93.3% and 99.6% ep according to method B. The product was further purified by slurring it in a mixture of toluene (100 mL) and isopropyl alcohol (2 mL) at room temperature for 3 h. The product (MSA salt of (R)-CN47583, compound of formula II, wherein $R^1$ is trifluoromethyl, $R^2$ is n-butyl, $R^8$ is 5-chloro, $R^9$ is hydrogen and $R^{10}$ is hydrogen) was filtered, washed with toluene (10 mL) and dried at 40° C. under vacuum. The product was obtained as white solid (17.1 g, 35.3 mmol, 59% yield) with a purity of 93.3% and 99.9% ep according to method B, and an assay of 92.8% w-/w according to $^1$H-NMR.

Example 20.2

S)-2-(2-Amino-5-chlorophenyl)-1,1,1-trifluorooct-3-yn-2-ol methanesulfonate (2:3 mol/mol Example 20.1 was repeated with (1R,2S)-PNE as chiral ligand to obtain the (S)-enantiomer of CN47583.

A solution of (1R,2S)-PNE (17.6%-w/w, 42.0 g, 36.0 mmol) in THF/toluene (9:1-w/w) was charged a vessel at room temperature. A solution of diethylzinc in toluene (29.9%-w/w, 12.0 g, 29.05 mmol) was added at 17 to 25° C. and the mixture was aged at said temperature for 30 min, 1-hexyne (97%-w/w, 13.21 g, 156.0 mmol, compound of formula III, wherein $R^2$ is n-butyl) was added at 18° C. and the resulting solution was aged at 20° C. for 60 min. A solution of BuLi in toluene (3.09 mol/kg, 35.53 g, 109.8 mmol) and a solution of 1-(2-amino-5-chlorophenyl)-2,2,2-trifluoroethanone (CN23315, a compound of formula IV, wherein $R^1$ is trifluoromethyl, $R^8$ is 5-chloro, $R^9$ is hydrogen and $R^{10}$ is hydrogen) in toluene/THF (1:1 w/w) (39.6%-w/w, 67.75 g, 120.0 mmol) were added in parallel to the reaction mixture at 20° C. within 3 h. The addition of BuLi was started 10 min in advance of the CN23315 addition. After completed addition of CN23315 the reaction mixture was stirred for 30 min at 20° C., then heated to 30° C. over a period of 60 min and aged for 6 h at 30° C. The reaction mixture was stirred at 0° C. overnight.

HPLC (Method B) indicated 81.9% conversion. The reaction mixture was diluted with toluene (51.6 g) and quenched by addition of aqueous citric acid solution (1 M, 88.2 g). After stirring for 15 min the phases were separated and the organic phase successively washed with water (18.1 g), aqueous NaHCO$_3$ solution (5%-w/w, 48.0 g) and water (24.0 g). The organic phase was partially concentrated (110 g residual solution), diluted with toluene (60 g), and partially concentrated again (114 g residue). The residue was diluted with toluene (120 g). Isopropyl alcohol (3.2 g) was added. Methanesulfonic acid (10.96 g, 114 mmol) was added at 30° C. over a period of 30 min and the mixture was stirred for 30 min. A second portion methanesulfonic acid (5.78 g, 60 mmol) was added at 30° C. over a period of 30 min. The mixture was stirred at 30° C. for 30 min, cooled to 5° C. over a period of 60 min, and aged at 5° C. for 30 min. The crystals were filtered, washed with cold toluene/isopropyl alcohol (98:1, 1×25 mL, 2×120 mL) and dried under vacuum at 40° C. The product (MSA salt of compound of formula II, wherein $R^1$ is trifluoromethyl, $R^2$ is n-butyl, $R^8$ is 5-chloro, $R^9$ is hydrogen and $R^{10}$ is hydrogen, 28.57 g) was obtained as slightly beige solid (96.5% w-/w assay according to $^1$H-NMR).

Example 21

(R)-6-Chloro-4-(hex-1-yn-1-yl)-4-(trifluoromethyl)-1,4-dihydro-2H-3,1-benzoxazin-2-one (R)-2-(2-Amino-5-chlorophenyl)-1,1,1-trifluorooct-3-yn-2-ol methanesulfonate ((R)-CN47583) obtained according to example 20.1 (92.8%-w/w as methanesulfonate 2:3 mol/mol, 15.0 g, 30.9 mmol) in ethyl acetate/heptanes (2:1-w/w, 30 g) was charged to a jacketed 150 mL-reactor with agitator and off-gas scrubber with caustic soda. The reaction mixture was cooled to 15° C. and aqueous Na$_2$CO$_3$ solution (12%-w/w, 27 g, formation of gas during addition!) was added, and then the mixture was stirred for 5 min at 15° C. The aqueous phase was separated and removed. Aqueous Na$_2$CO$_3$ solution (12%-w/w, 33 g) was added to the organic phase. Triphosgene (3.62 g, 12.2 mmol) was added in portions over a period of 25 min at 7 to 15° C. The reaction mixture was stirred for 15 min at 8° C. and sampled for conversion control (conversion more than 99% according to method C). The phases were separated. The organic phase was dried over MgSO$_4$, filtered and concentrated under vacuum to dryness. The crude product (11.4 g) was obtained as yellow oil (purity more than 99.0% according to method C). A sample was cooled to 5° C. and it slowly solidified. The crude product was slurried in hexane (10 mL) for 2 h at room temperature. The product was filtered, washed with cold (approx. 5° C.) hexane (5 mL) and dried at 30° C. under vacuum. The product ((R)-compound of formula I, wherein $R^1$ is trifluoromethyl, $R^2$ is n-butyl, $R^8$ is 6-chloro, $R^9$ is hydrogen and $R^{10}$ is hydrogen) was obtained as white solid (7.73 g, 22.7 mmol, 73% yield) with a purity of more than 99.0% according to method C and an assay of 97.1%-w/w according to $^1$H-NMR. Concentration of the mother liquor to dryness under vacuum afforded additional product as yellow solid (2.54 g, 7.2 mmol, 23% yield) with a purity of 98% according to method C and an assay of 93.6%-w/w according to $^1$H-NMR.

Example 22

(S)-6-Chloro-4-(hex-1-yn-1-yl)-4-(trifluoromethyl)-1,4-dihydro-2H-3,1-benzoxazin-2-one (S)-2-(2-Amino-5-chlorophenyl)-1,1,1-trifluorooct-3-yn-2-ol methanesulfonate ((S)-CN47583) obtained according to example 20.2 (96.5%-w/w as methanesulfonate 2:3 mol/mol, 15.0 g, 32.2 mmol) in ethyl acetate/heptanes (2:1-w/w, 30 g) was charged to a jacketed 150 mL-reactor with agitator and off-gas scrubber with caustic soda. The reaction mixture was cooled to 15° C. and aqueous $Na_2CO_3$ solution (12%-w/w, 27 g, formation of gas during addition!) was added, and then the mixture was stirred for 5 min at 15° C. The aqueous phase was removed. And aqueous $Na_2CO_3$ solution (12%-w/w, 33 g) was added to the organic phase. A solution of triphosgene (0.73 g, 2.5 mmol) in diphosgene (2.90 g, 14.7 mmol) was added to the reaction mixture over a period of 30 min at 7 to 11° C. The reaction mixture was stirred at 8° C. for 20 min. The reaction mixture was sampled for conversion control until a conversion of more than 99% was reached (according to method C). The phases were allowed to separate. The aqueous phase was removed. The organic phase was dried over $MgSO_4$, filtered and concentrated to dryness. The crude product (10.5 g, 31.1 mmol, 97% yield) was obtained as yellow solid (purity>99.0%, HPLC method C, 98.6%-w/w assay by $^1$H-NMR). The crude product was slurried in hexane (10 mL) for 3 h at room temperature. The product was filtered, washed with cold (approx. 5° C.) hexane (5 mL) and dried at 30° C. under vacuum. The product ((S)-compound of formula I, wherein $R^1$ is trifluoromethyl, $R^2$ is n-butyl, $R^8$ is 6-chloro, $R^9$ is hydrogen and $R^{10}$ is hydrogen) was obtained as white solid (8.25 g, 24.6 mmol, 77% yield) with a purity of more than 99.0% (according to method C) and assay 99.1%-w/w according to $^1$H-NMR. Concentration of the mother liquor to dryness under vacuum afforded additional product as yellow solid (1.58 g) with a purity of 97% (according to method C).

Example 23

Cyclisation of SD573 (Free Base) with Diphosgene in Triphosgene

Triphosgene (5.12 g, 17 mmol) was added to diphosgene (20.16 g, 101 mmol) at 8° C. and the mixture was aged under rigorous stirring for 30 min (until all triphosgene was dissolved).

In another vessel, aqueous $Na_2CO_3$ (12%-w/w, 235 g, 266 mmol) was charged at 8° C. to SD573 free base (compound of formula II, wherein $R^1$ is trifluoromethyl, $R^2$ is cyclopropyl, $R^8$ is 5-chloro, $R^9$ is hydrogen and $R^{10}$ is hydrogen, 67.0 g, 0.231 mol) in heptane (68.3 g) and ethyl acetate (136.1 g). Then the solution of triphosgene in diphosgene was added at 8 to 11° C. within 90 min. The mixture was aged further 45 min at 8° C. The mixture was warmed to 15° C. within ca. 30 min and aged further 30 min at 15° C., total conversion was reached according to Method C. Heptane (137 g) was added at 15° C. and the mixture was aged for further 60 min at 15° C. The mixture was warmed to 19° C. and water (80 g) was added. The phases were separated and the aqueous phase was removed. The organic phase was distilled and heptane continuously added until 5.4-w/w % of ethyl acetate remained (concentration of the heptane solution was approx. 9.5 mL/g of SD573). The mixture was seeded at 58° C. with DMP-266 (0.8 g) and the suspension was stirred further 120 min at 58° C., cooled to 25° C. within 120 min, cooled to −13° C. within 120 min, stirred further ca. 30 min at −13° C. and filtered. The wet cake was washed at −8° C. two times with heptane (pre-cooled at −8° C., 50 mL). The cake was dried for 8 h at 80° C. under vacuum. 90.2% yield (65.99 g, 209 mmol) of product (DMP-266, compound of formula I, wherein $R^1$ is trifluoromethyl, $R^2$ is cyclopropyl, $R^8$ is 6-chloro, $R^9$ is hydrogen and $R^{10}$ is hydrogen) were obtained with a purity of 100%-w/w according to Method D. Crystal form I was obtained according to X-ray analysis.

Comparative Example 1

Cyclisation of SD573 with Triphosgene, Homogeneous

Aqueous $Na_2CO_3$ (10.6 g, 0.126 mol) was charged at 25° C. to SD573 free base (25.13 g, 0.087 mol) in acetonitrile (25 mL) in a 500 mL-reactor. The mixture was cooled to −12° C. and a solution of triphosgene in acetonitrile (19.7%-w/w, 63.63 g, 42 mmol) was added within 40 min at −10 to −5° C. After 90 min a total conversion was reached according to Method C. The reaction mixture was heated to 25° C., neutralized at 20° C. to 25° C. with $Na_2CO_3$, washed with water and then filtered. The mixture was cooled to −10° C. and water (7.5 g) was added dropwise. The slurry was filtered and the product was isolated. The wet cake was dried in vacuo to give the final product with 5% yield (1.89 g, 6 mmol). The purity was 97.3%-w/w according to Method D.

Comparative Example 2

Cyclisation of SD573 with Triphosgene, Homogenous

To SD573 free base (25.04 g, 0.086 mol) dissolved in acetone (25 mL) in a 500 mL-reactor, $Na_2CO_3$ (10.6 g, 0.126 mol) and water (50 mL) were charged at 25° C. The mixture was cooled to −12° C. and a solution of triphosgene in acetonitrile (24%-w/w, 52 g, 42 mmol) was added at −10 to −5° C. within 55 min. After 60 min a conversion of 98.1%-w/w was reached, according to Method C. The reaction mixture was heated to 25° C. After further 100 min a conversion of 98.8%-w/w was reached, according to Method C. Triphosgene (0.69 g) was added. After 180 min a total conversion was reached, according to Method C. The reaction mixture was neutralized at 20° C. to 25° C. with $Na_2CO_3$ and then filtered. The filter was washed with water (12.5 g). To the filtrate water (100 mL) was added at 25° C. Because after 15 h no product precipitated, the mixture was cooled to −10° C. and filtered to obtain crop 1. To the filtrate water (200 mL) was added at −10° C. and the suspension was filtered again to obtain crops 2. Precipitation was repeated with further water (100 mL) addition to the filtrate of crop 2 to obtain crop 3. The combined crops (1 to 3) of wet product were dried in vacuo to obtain 84.5% yield (22.39 g, 71 mmol). The purity was 96.9%-w/w according to Method D.

Comparative Example 3

Cyclisation of SD573 with Triphosgene, Homogenous

To SD573 free base (25.11 g, 0.087 mol) dissolved in THF (25 mL) in a 500 mL-reactor, $Na_2CO_3$ (10.6 g, 0.126 mol) and water (50 mL) was charged at 25° C. The mixture was cooled to −12° C. and a solution of triphosgene in THF (22.1%-w/w, 56.5 g, 42 mmol) was added between −10° C. to −5° C. within 36 min. After 120 min a conversion of 96.2%-w/w was reached, according to Method C. The reaction mixture was heated to 25° C. After further 100 min a conversion of 97.7% (w/w) was reached, according to Method C. Triphosgene (0.68 g) was added. Further small portions of triphosgene were added until 99.6% (w/w) conversion was reached. The reaction mixture was neutralized between 20 to 25° C. with $Na_2CO_3$ and then filtered. To the mixture water (325 g) was added at 25° C.

The mixture was cooled to 0° C. and filtered (crop 1). To the product remaining in the vessel further water (200 mL) was added at 5° C.; and the mixture was filtered (crop 2). To the product remaining in the vessel further water (100 mL) was added at 5° C.; and the mixture was filtered (crop 3). The combined crops (1 to 3) of wet product were dried in vacuo to obtain 56.5% yield (15.53 g, 49 mmol). The purity was 98.1%-w/w according to Method D.

Comparative Example 4

Cyclisation of SD573 with Triphosgene

Aqueous $Na_2CO_3$ (21.5 g, 0.256 mol, in 100 mL of water) was charged at 25° C. to SD573 free base (50.1 g, 174 mmol) in acetonitrile (50 mL) in a 1 L reactor. After the $Na_2CO_3$ addition the used equipment which contained the SD573 free base was rinsed with 10 mL of water. The mixture was cooled to −12° C. and a solution of triphosgene in acetonitrile (24.3%-w/w, 103.3 g, 84 mmol) was added within 30 min at −10 to −5° C. The solution of triphosgene in acetonitrile as described in WO2010/032259A example 1 was too concentrated, all triphosgene was not dissolved, therefore after the triphosgene addition the used equipment which contained the triphosgene was rinsed with 5 mL of acetonitrile. After 60 min at −12° C. the mixture was warmed to 25° C. and total conversion was reached according to Method C. Water (65 mL) to reach the same dilution as described in WO2010/032259A was added at 25° C. Contrary to the teaching of WO2010/032259A no precipitation occurred at 10° C., so the mixture was cooled to −5° C. and then filtered. To remove the product completely, the reactor was rinsed with water (200 mL), which was used afterwards to wash the wet filter cake. The filter cake was dried in vacuo to give the final product with 34.2% yield (18.63 g, 6 mmol). The purity was 100%-w/w according to Method D.

Analytical Methods:

Method A: (HPLC Method Used for the Determination of the Enantiomeric Purity) Column: Chiralpak® AD, 250×4.6 mm; Temperature: 40° C.; Flow: 1.0 mL/min; Mobile Phase: hexane/isopropyl alcohol=75:25 (v/v); UV Detection: 260 nm Method B: (HPLC Method Used for Conversion, Purity and Enantiomeric Purity):

Column: Chiralpak® AD-H, 250×4.6 mm; Temperature: 40° C.; Flow: 1.0 mL/min; Mobile phase: hexane/isopropyl alcohol=89:11 (v/v); UV Detection: 260 nm Method C: (HPLC Method Used for the Determination of the Purity):

Column: Zorbax® RX-C18, 250×4.6 mm, 5 micrometer; Temperature: 40° C.; Flow: 1.5 mL/min; Mobile phase A: 50%-w/w buffer/50%-w/w MeCN; Mobile phase B: MeCN; Buffer: 0.1%-w/w $H_3PO_4$ in water, pH adjusted to 3.6; Gradient: 0 min 0%-w/w B to 30 min 90%-w/w B; UV Detection: 250 nm Method D: (HPLC Method Used for the Determination of the Purity):

Column: Zorbax® SB-CN, 150×4.6 mm; Temperature: 40° C.; Flow: 1.5 mL/min; Mobile phase A: 90%-w/w water/10%-w/w MeOH+0.05%-w/w TFA (v/v); Mobile phase B: 90% water/10%-w/w MeOH+0.05%-w/w TFA (v/v); Gradient: 16 min 40%-w/w to 50% B, 7 min to 65%-w/w B, 5 min to 70% B, 1 min to 80% of B, 2 min hold 80%-w/w B, 1 min to 40%-w/w B; UV Detection: 250 nm

The invention claimed is:
1. A process for the preparation of a compound of formula

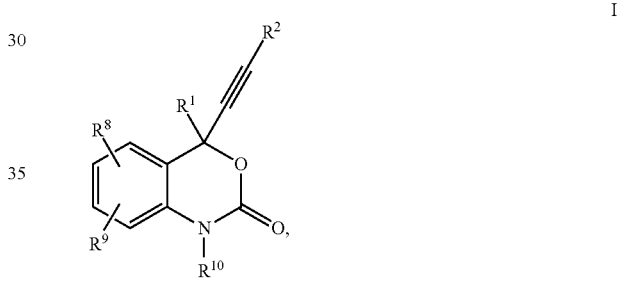

and/or a suitable salt thereof,
wherein
$R^1$ is selected from the group consisting of hydrogen, linear or branched $C_{1-6}$-alkyl or ($C_{1-6}$-alkoxy)carbonyl, any alkyl or alkoxy optionally being substituted with one or more halogen atoms,
$R^2$ is selected from the group consisting of linear or branched $C_{1-6}$-alkyl,
($C_{1-6}$-alkoxy)carbonyl, $C_{3-6}$-alkenyl, $C_{3-6}$-alkynyl and $C_{3-6}$-cycloalkyl, wherein each alkyl, alkoxy, alkenyl, alkynyl and cycloalkyl can carry a further substituent selected from the group consisting of aryl, aralkyl, $C_{1-6}$-alkyl and (1'-$R^3$)—$C_{3-6}$-cycloalkyl, wherein $R^3$ is hydrogen, methyl or ethyl, and wherein any alkyl, cycloalkyl, aryl, and aralkyl is optionally substituted with one or more halogen atoms, cyano, $C_{1-6}$-alkyl, $C_{3-6}$-cycloalkyl, —$NR^4R^5$, —$SR^6$, $S(O)$ $R^6$ or $S(O_2)R^6$, and/or —$OR^7$, with $R^6$ is $C_{1-6}$-alkyl,
optionally substituted with one or more halogen atoms,
$R^7$ is hydrogen or $C_{1-6}$-alkyl, optionally substituted with one or more halogen atoms, where
(a) $R^4$ and $R^5$ are independently selected from hydrogen or $C_{1-6}$-alkyl, or
(b) $R^4$ is hydrogen and $R^5$ is $C_{2-7}$-acyl or ($C_{1-6}$-alkoxy) carbonyl, wherein each acyl and alkoxy in $R^5$ in turn is optionally substituted with one or more halogen atoms, or (c) $R^4$ and $R^5$ together with the nitrogen atom form a 5 to 7 membered heterocyclic ring, or
(d) $R^4$ and $R^5$ together are =CH-aryl, the aryl moiety optionally being substituted with one or more substituents selected from halogen atoms, —NH2, —NH($C_{1-6}$-alkyl), —N($C_{1-6}$-alkyl)$_2$ or $C_{1-6}$-alkyl, or
(e) $R^4$ and $R^5$ together are =CH—N($C_{1-6}$-alkyl)$_2$,
$R^6$ is $C_{1-6}$-alkyl, optionally substituted with one or more halogen atoms, and
$R^7$ is hydrogen or $C_{1-6}$-alkyl, optionally substituted with one or more halogen atoms,
$R^8$ and $R^9$ are independently selected from the group consisting of hydrogen, halogen atom, and $C_{1-6}$-alkyl optionally substituted with one or more halogen atoms,
$R^{10}$ is hydrogen or a group selected from the group consisting of aryl, aralkyl, $C_{1-6}$-alkyl and ($C_{1-6}$-alkoxy)carbonyl, wherein the aryl moiety in any aryl or aralkyl is optionally substituted with one or more substituents selected from $C_{1-6}$-alkyl, $C_{1-6}$-alkoxy or $C_{1-6}$-cycloalkyl, each alkyl, alkoxy or cycloalkyl substituent is optionally substituted with one or more halogen atoms,
said process comprising the reaction of a compound of formula

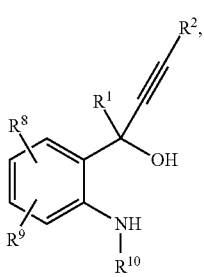

and/or a suitable salt thereof,
wherein $R^1$, $R^2$, $R^8$, $R^9$ and $R^{10}$ are as defined above,
with a cyclisation agent selected from phosgene, diphosgene, triphosgene and mixtures thereof,
wherein the reaction is carried out in the presence of an aqueous base and a water-immiscible organic solvent, wherein at least 90% of said organic solvent consists of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane.

2. The process of claim 1, wherein the cyclisation agent is provided in gaseous form.
3. The process of claim 1, wherein the cyclisation agent is provided in liquid form.
4. The process of claim 1, wherein the cyclisation agent is provided in solid form.
5. The process of claim 1, wherein the molar ratio of the cyclisation agent, calculated in molar equivalents of phosgene, to the compound of formula II is in a range from 1:1 to 4:1.
6. The process of claim 1, wherein the weight ratio of water to the organic solvent(s) is in the range from 1:1 to 5:1.
7. The process of claim 1, wherein at least 90% of said organic solvent consists of at least one compound selected from the group consisting of $C_{2-5}$-alkyl $C_{2-5}$-carboxylates and mixtures of at least one $C_{2-5}$-alkyl $C_{2-5}$-carboxylate with at least one $C_{5-8}$-alkane.

8. The process of claim 1, wherein the $C_{2-5}$-alkyl $C_{2-5}$-carboxylate is selected from the group consisting of $C_{2-5}$-alkyl acetates, $C_{2-5}$-alkyl propionates, and $C_{2-5}$-alkyl butyrates.
9. The process of claim 1, wherein the $C_{2-5}$-alkyl $C_{2-5}$-carboxylate is selected from the group consisting of $C_{2-5}$-alkyl acetates and $C_{2-5}$-alkyl propionates.
10. The process of claim 1, wherein the $C_{5-8}$-alkane is selected from the group consisting of pentanes, cyclopentane, hexanes, cyclohexane, heptanes, cycloheptane and octanes.
11. The process of claim 1, wherein the $C_{5-8}$-alkane is selected from the group consisting of hexanes, cyclohexane, heptanes and cycloheptane.
12. The process of claim 1, wherein the reaction is carried out at a temperature from −30 to +40° C.
13. The process of claim 1, wherein the reaction is carried out at a temperature from 0 to +20° C.
14. The process of claim 1, wherein the compound of formula

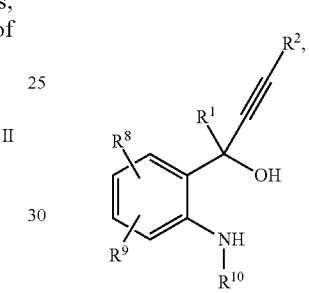

wherein $R^1$, $R^2$, $R^8$, $R^9$, $R^{10}$ and are as defined above,
is obtained by a process comprising the steps of
(i) reacting a protic chiral auxiliary with a diorganylzinc(II) compound, in the presence of an aprotic solvent, at a temperature in the range of 0 to 40° C., and
(ii) keeping the mixture of step (i), preferably under stirring, in a first maturation period until the reaction is completed, but of at least 20 min, and
(iii) reacting the mixture obtained after step (ii) with a compound of formula

wherein $R^2$ is as defined above, and
(iv) keeping the mixture of step (iii), preferably under stirring, in a second maturation period until the reaction is completed, but of at least 10 min, and
(v) reacting the mixture obtained after step (iv) with a compound of formula

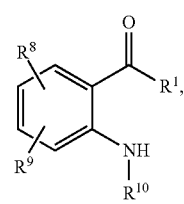

wherein R¹, R⁸, R⁹ and R¹⁰ are as defined above, and an organolithium base and/or the other alkali metal organyl, at a temperature in the range of 0 to 40° C., and (vi) keeping the mixture obtained in step (v) to 10 to 50° C. until the reaction is completed, to obtain the compound of formula II.

15. The process of claim 14, wherein the protic chiral auxiliary is selected from the group consisting of N,N-disubstituted ephedrine derivatives.

16. The process of claim 14, wherein the molar ratio of the protic chiral auxiliary to the diorganylzinc(II) compound is in the range of 1.5:1 to 1:1.

17. The process of claim 14 wherein the diorganylzinc(II) compound is selected from the group consisting of di($C_{1-8}$-alkyl) and di($C_{3-6}$-cycloalkyl), wherein the alkyl moieties are selected from the group consisting of methyl, ethyl, propyl, isopropyl, butyl, isobutyl, sec-butyl and tert-butyl, pentyl, hexyl, heptyl, and octyl, and wherein the cycloalkyl moieties are selected from the group consisting of cyclopropyl, cyclobutyl, cyclopentyl and cyclohexyl.

18. The process of claim 14, wherein in step (i) the molar ratio of the protic chiral auxiliary to the compound of formula IV is in the range of 1:1 to 1:10.

19. The process of claim 14, wherein in step (iii) the compound of formula III is used in a molar ratio to the compound of formula IV of 1:0.6 to 1:1.3.

20. The process of claim 14, wherein the organolithium base and/or the other alkali metal organyl is added in a molar ratio to the compound of formula IV from 1:0.8 to 1:1.5.

21. The process of claim 14, wherein the organolithium base is selected from the group consisting of ($C_{1-6}$-alkyl) lithium, lithium diisopropylamide (LDA), lithium hexamethyldisilazide (LiHMDS), phenyllithium, and naphthyllithium.

22. The process of claim 21, wherein the ($C_{1-6}$-alkyl) lithium is selected from the group consisting of methyllithium, n-butyllithium, sec-butyllithium, tert-butyllithium, and hexyllithium.

23. The process of claim 1, wherein the other alkali metal organyl is selected from sodium or potassium $C_{1-6}$-alkoxides, sodium or potassium diisopropylamine, and sodium or potassium hexamethyldisilazide.

24. The process of claim 14, wherein the temperature during the addition of the base is of from +10 to +30° C.

25. The process of claim 14, wherein the aprotic solvent is selected from the group consisting of aprotic non-polar solvents, aprotic polar solvents and mixtures thereof.

26. The process of claim 1, wherein the molar ratio of the cyclisation agent, calculated in molar equivalents of phosgene, to the compound of formula II is in a range from 1:1 to 2.5:1.

27. The process of claim 1, wherein the $C_{5-8}$-alkane is heptanes.

28. The process of claim 14, wherein in step (i) the molar ratio of the protic chiral auxiliary to the compound of formula IV is in the range of 1:2 to 1:6.

29. The process of claim 14, wherein in step (i) the molar ratio of the protic chiral auxiliary to the compound of formula IV is in the range of 1:3 to 1:6.

* * * * *